US009850495B2

(12) United States Patent
Allen et al.

(10) Patent No.: US 9,850,495 B2
(45) Date of Patent: Dec. 26, 2017

(54) NUCLEOTIDE SEQUENCES ENCODING FASCIATED EAR4 (FEA4) AND METHODS OF USE THEREOF

(71) Applicants: E I DU PONT DE NEMOURS AND COMPANY, Wilmington, DE (US); COLD SPRING HARBOR LABORATORY, Cold Spring Harbor, NY (US); IOWA STATE UNIVERSITY RESEARCH FOUNDATION, INC., Ames, IA (US)

(72) Inventors: Stephen M Allen, Wilmington, DE (US); David Peter Jackson, New York, NY (US); Mai Komatsu, Wilmington, DE (US); Michael Pautler, Cold Spring Harbor, NY (US); Hajime Sakai, Newark, DE (US); Erik Vollbrecht, Ames, IA (US); Rebecca Weeks, Ames, IA (US)

(73) Assignees: E. I. du Pont de Nemours And Company, Wilmington, DE (US); Cold Spring Harbor Laboratory, Cold Spring Harbor, NY (US); Iowa State University Research Foundation, Inc., Ames, IA (US)

(*) Notice: Subject to any disclaimer, the term of this patent is extended or adjusted under 35 U.S.C. 154(b) by 341 days.

(21) Appl. No.: 14/384,695

(22) PCT Filed: Mar. 14, 2013

(86) PCT No.: PCT/US2013/031145
§ 371 (c)(1),
(2) Date: Sep. 12, 2014

(87) PCT Pub. No.: WO2013/138544
PCT Pub. Date: Sep. 19, 2013

(65) Prior Publication Data
US 2015/0033415 A1    Jan. 29, 2015

Related U.S. Application Data

(60) Provisional application No. 61/610,730, filed on Mar. 14, 2012, provisional application No. 61/759,342, filed on Jan. 31, 2013.

(51) Int. Cl.
| | |
|---|---|
| C12N 15/87 | (2006.01) |
| C12N 15/82 | (2006.01) |
| A01H 5/10 | (2006.01) |
| C07K 14/415 | (2006.01) |
| C12Q 1/68 | (2006.01) |

(52) U.S. Cl.
CPC ......... *C12N 15/8261* (2013.01); *A01H 5/10* (2013.01); *C07K 14/415* (2013.01); *C12N 15/8216* (2013.01); *C12N 15/8229* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS
2008/0229439 A1    9/2008    La Rosa et al.
2009/0094717 A1    4/2009    Troukhan et al.

FOREIGN PATENT DOCUMENTS
| WO | 01/70987 A2 | 9/2001 |
| WO | WO 01/70987 A2 * | 9/2001 |

OTHER PUBLICATIONS

McCallum et al (2000, Plant Physiology 123:439-442).*
Jennifer C. Fletcher et al., Signaling of Cell Fate Decisions by CLAVAT3 in Arabidopsis Shoot Meristems, Science, Mar. 19, 1999, pp. 1911-1914, vol. 283.
Thomas R. Mertens et al., The Morphology, Anatomy, and Genetics of a Stem Fasciation in Lycopersicon esculentum, American Journal of Botany, Nov. 1954, p. 726-732, vol. 41, No. 9.
Eugene J. Szymkowiak et al., The Internal Meristem Layer (L3) Determines Floral Meristem Size and Carpel Number in Tomato Periclinal Chimeras, The Plant Cell, Sep. 1992, pp. 1089-1100, vol. 4.
Funio Taguchi-Shiobara et al., The fasciated ear2 gene encodes a leucine-rich repeat receptor-like protein that regulates shoot meristem proliferation in maize, Genes & Development, 2001, pp. 2755-2766, vol. 15.
Amy E. Trotochaud et al., The CLAVATA1 Receptor-like Kinase Requires CLAVATA3 for Its Assembly into a Signaling Complex That Includes KAPP and a Rho-Related Protein, The Plant Cell, Mar. 1999, pp. 393-405, vol. 11.
Yonghong Wang et al., Genes controlling plant architecture, Current Opinion in Biotechnology, 2006, pp. 123-129, vol. 17.
Etsuo Yamamoto et al., Molecular characterization of two soybean homologs of Arabidopsis thaliana CLAVAT1 from the wild type and fasciation mutant, Biochimica et Biophysica Acta, 2000, pp. 333-340, vol. 1491.
International Search Report—PCT/US2013/031145—dated May 21, 2013.
National Center for Biotechnology Information GI No. Q9SX27, PAN_ARATH, May 1, 2000, Sequence Version 1.
National Center for Biotechnology Information GI No. XP_002438208, C5Z847_SORBI, Sep. 1, 2009, Sequence Version 1.
National Center for Biotechnology Information GI No. Q5Z6N9.1, A3BAH7_ORYSJ, Mar. 20, 2007, Sequence Version 1.

* cited by examiner

*Primary Examiner* — Stuart F Baum
(74) *Attorney, Agent, or Firm* — Ballard Spahr LLP

(57) ABSTRACT

Methods and compositions for modulating shoot apical meristem size are provided. Methods are provided for modulating the expression of Fea4 sequence in a host plant or plant cell to modulate agronomic characteristics such as altered size and number of organs, including plant seeds.

4 Claims, 9 Drawing Sheets

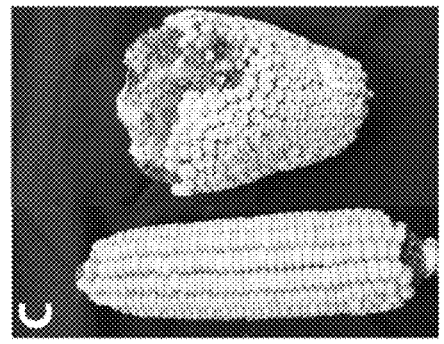
FIG. 2A FIG. 2B FIG. 2C
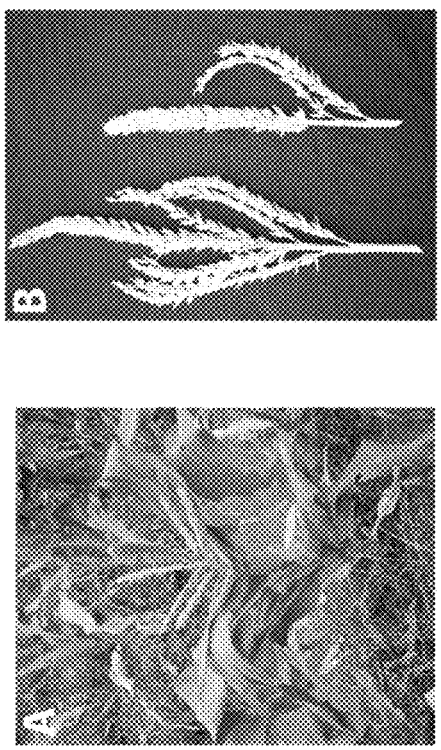
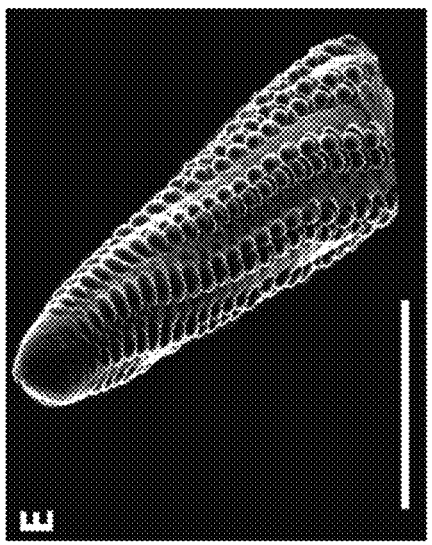
FIG. 2E
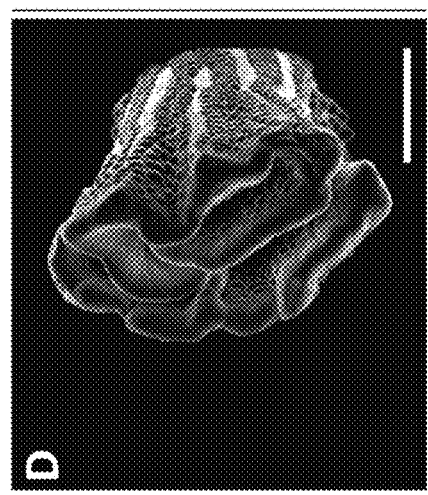
FIG. 2D

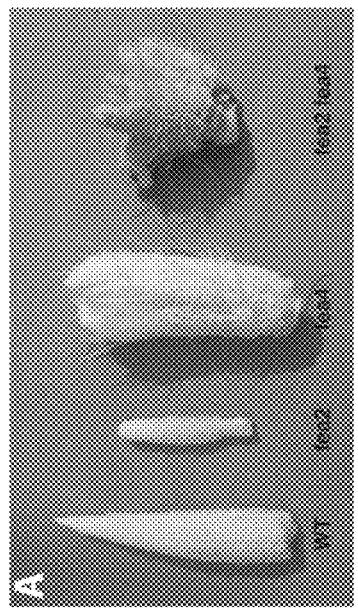
FIG. 4A
FIG. 4B fea4 (A619)

A619 WT

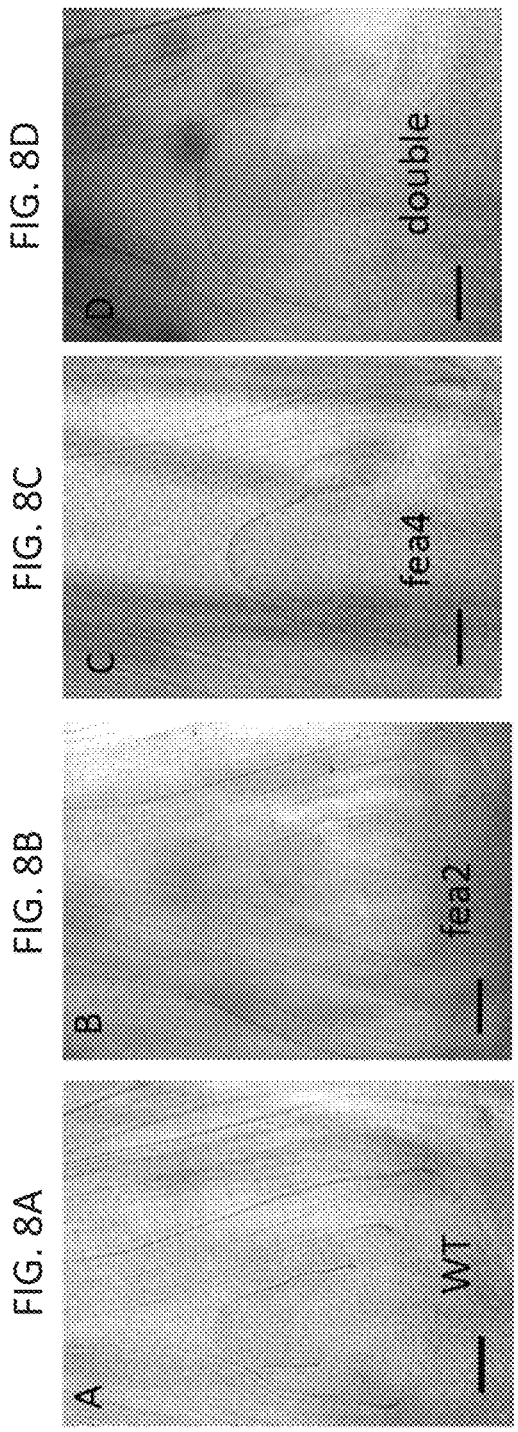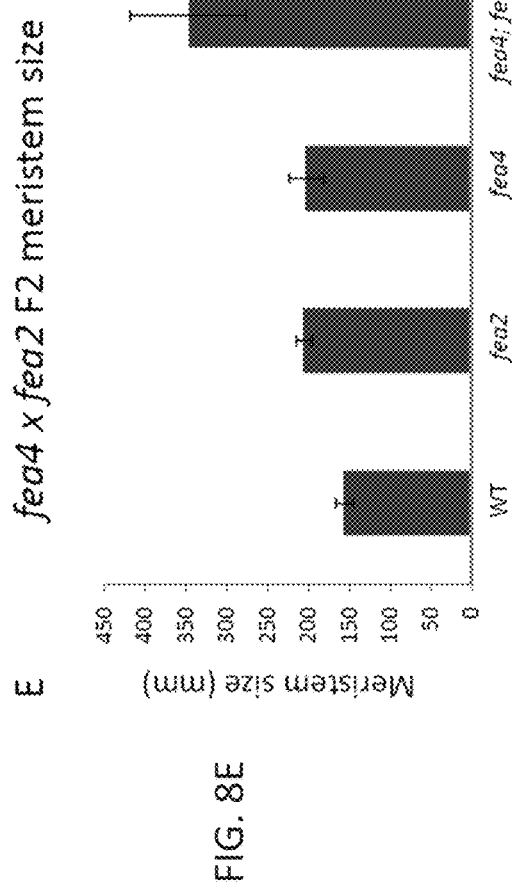

SEQUENCE LISTING

```
<160> NUMBER OF SEQ ID NOS: 20

<210> SEQ ID NO 1
<211> LENGTH: 2766
<212> TYPE: DNA
<213> ORGANISM: Zea mays

<400> SEQUENCE: 1
tcttcatcaa atttgcgcgg cgtctgcgtt ccctgcttcc cattcgaaaa caaaagcaaa      60
aggtgcgcat tcacggtgtc gccctcgtct ctactcgtgt ctcgtcttgg gtagcgtacg     120
caccttagct cgcaaccatc catccatcca cggggctcgg gcgcagcagc ctccccgtc     180 gtcgtcttcg tcgtcgcctt gccgccgctc tgatccgtgc ccgatgcatc gtcagccatc     240
tcctcacgcc ttcaggtagt aaaagtatac taagccgcag ggcaccacaa cgcaacacgt     300
ggtgcctgcc tgcctccttc cttgttcgct ttgcggcgcg agcgttttgt ctgttgttgt     360
ctcccttggg accggcgcgt ccggctggct cactaccact aacgtgttgt tgcctgcctt     420
gtgcggcgcc cgtggttcgc attgcgtttg cagcagcagc ggcagctggg cggagcaggg     480
cgcgggcggg taccgccacg gcagggacgg cgccaccttc ctcctccccg agctcctcca     540
gcgcagtaat aacgccgccc tgcccttgt ttatccgcct gcctgcgtat tttgtttcct     600 ttcttttct tcttgttgga tttctcatgg ctgttggttg cacgcgcgcg catcgcgggg     660
gctaatgtga aggccccaac cccagctcca agtcctccag cgccgccacc ttcgtgccgc     720
cgctcgccgc cgcggtgagt tcactgactg agaatgagat acggttcgtt ctccgccgcg     780
gcttcttcac tttgagcgtg aatgacatgg aggctctctc tggcgtcttt ttgtctgcag     840
catggaggag gagtagcggc cccgtttggc atggcgccgc tgggagtggc ggcggcggac     900
gaagcccggt tctgcatgac gccgtggtca gcggcggcgc acttcgagaa ctggggcgac     960
tccggcatcg tcgtcaccag cccgctcgcc gagacggcct ccaccgacgt cgacatggtc    1020
```

-continued

| | |
|---|---|
| tgctcctcaa tactcagctt ccatccatct tcatccgcat gcacagtata tatgcctgcc | 1080 |
| atgaactccg cctggagtat atgtatatgc cgtgacgtgt gactccaccg ccgtcgtcgt | 1140 |
| agggtggagg tggagccatg gcgcagagcg tcgacggaca tgacaactca ttgccggcgt | 1200 |
| gcaaggtgga gcccagggat cacaaggtgc gctatgccat gtcacgtgaa cacgtcgtcg | 1260 |
| tggtcccaaa aaggaactag aagagcagca gatgtgattg tggttttgt gctgtgtcat | 1320 |
| ggcaggcgca gaggaggctt gcgcaaaacc gcgaggcggc ccggaaaagc cggatgagga | 1380 |
| agaaggtgat ccccttccc ctcacgggaa gcttctgtac attatgctat gcttgcaagt | 1440 |
| tgcattccat cctgtcttct tcttgctcag tacccccctg tttatttacc ctgacgggag | 1500 |
| gcttactgag ttttgtctac agttttactg taccatgctg tcactgtttc cacttgcaag | 1560 |
| atcgctgaag cactgtgcaa attcgctctg taggcgtaca ttgtggagct ggaaaacagc | 1620 |
| cggtccaagc tgtcccatct tgagcaggag cttcaaaggg caaggcagca ggtgaactcc | 1680 |
| tgatctgttt tcctctgaag aacgaaacga tccatactac ttcgacgctg attgtctatg | 1740 |
| ggctgtaaat acaggggatg ttcattgcaa gtggacgctc cggagatcat ggatgctcca | 1800 |
| ctggaggcag atgatctttt tttcttctct tttacattgc tcagctcttg ttctctgaat | 1860 |
| tctgatcctg tgcaatgtaa agcctaacct gtgtccttgc aggtgcgttg gcgttcgacc | 1920 |
| tggagtacgc gcggtggctg gacgagcacc agcaccacat gaacgacctc cgggtggccc | 1980 |
| tgagcgcgca gatcggcgac gacgacctgg gcgtgctggt ggacggcgcg atgctgcact | 2040 |
| acgaccagat gttccggctc aagggcgtgg ccacgaggac ggacgtgttc cacgtgctgt | 2100 |
| cgggcatgtg gatgagcccc gcggagcggt tcttcatgtg gctgggcggg ttccggtcgt | 2160 |
| cggagctgct caaggtgctg gcgcggcacg tggagccgct gacggagcag cagctggtgg | 2220 |
| gcatctgcgg cctgcagcag tcgctgcagc aggccgagga cgcgctgtcg caggggatgg | 2280 |
| aggccctgca gcaggccctc ggggacacgc tcgccgccgc cgccacgccg tgcgccgccg | 2340 |
| acagcgtcac caactacatg ggccagatgg ccgtcgccat gagcaagctc gccaccgtgg | 2400 |
| agaacttcct ccgccaggcg gacctgctgc ggcagcagac gctgaagcag gtgcgccgga | 2460 |
| tcctgaccac gcgccaagcc gcgcgcgcgc tgctcgtcat cagtgactac ttctcgcggc | 2520 |
| tccgtgcgct cagctccctg tggctgacgc ggccgacgga ttgattcggc gtaggcacac | 2580 |
| ggacgggagc tgtcgttggt tggttgcgct gagactgtaa tctgtatccg ttgtgagatg | 2640 |
| gggtgaccat gcggattcat caggcagaaa cggcgaatgt gtctagcttt agttttggct | 2700 |
| accattcagc ttcatcagtg aggctagagt agagcgattt cggtgcgcat gtccaggctt | 2760 |
| ttgctc | 2766 |

<210> SEQ ID NO 2
<211> LENGTH: 1299
<212> TYPE: DNA
<213> ORGANISM: Zea mays

<400> SEQUENCE: 2

| | |
|---|---|
| atgcatcgtc agccatctcc tcacgccttc agcagcagcg gcagctgggc ggagcagggc | 60 |
| gcgggcgggt accgccacgg cagggacggc gccaccttcc tcctccccga gctcctccag | 120 |
| cgcagcccca accccagctc caagtcctcc agcgccgcca ccttcgtgcc gccgctcgcc | 180 |
| gccgcgcatg gaggaggagt agcggccccg tttggcatgg cgccgctggg agtgcggcg | 240 |
| gcggacgaag cccggttctg catgacgccg tggtcagcgg cggcgcactt cgagaactgg | 300 |

```
ggcgactccg gcatcgtcgt caccagcccg ctcgccgaga cggcctccac cgacgtcgac    360
atgggtggag gtggagccat ggcgcagagc gtcgacggac atgacaactc attgccggcg    420
tgcaaggtgg agcccaggga tcacaaggcg cagaggaggc ttgcgcaaaa ccgcgaggcg    480
gcccggaaaa gccggatgag gaagaaggcg tacattgtgg agctggaaaa cagccggtcc    540
aagctgtccc atcttgagca ggagcttcaa agggcaaggc agcagggat gttcattgca     600 agtggacgct ccggagatca tggatgctcc actggaggtg cgttggcgtt cgacctggag    660
tacgcgcggt ggctggacga gcaccagcac cacatgaacg acctccgggt ggccctgagc    720
gcgcagatcg gcgacgacga cctgggcgtg ctggtggacg gcgcgatgct gcactacgac    780
cagatgttcc ggctcaaggg cgtggccacg aggacggacg tgttccacgt gctgtcgggc    840
atgtggatga gccccgcgga gcggttcttc atgtggctgg gcgggttccg gtcgtcggag    900
ctgctcaagg tgctggcgcg gcacgtggag ccgctgacgg agcagcagct ggtgggcatc    960
tgcggcctgc agcagtcgct gcagcaggcc gaggacgcgc tgtcgcaggg gatggaggcc   1020
ctgcagcagg ccctcgggga cacgctcgcc gccgccgcca cgccgtgcgc cgccgacagc   1080
gtcaccaact acatgggcca gatggccgtc gccatgagca agctcgccac cgtggagaac   1140
ttcctccgcc aggcggacct gctgcggcag cagacgctga agcaggtgcg ccggatcctg   1200
accacgcgcc aagccgcgcg cgcgctgctc gtcatcagtg actacttctc gcggctccgt   1260
gcgctcagct ccctgtggct gacgcggccg acggattga                          1299
```

<210> SEQ ID NO 3
<211> LENGTH: 432
<212> TYPE: PRT
<213> ORGANISM: Zea mays

<400> SEQUENCE: 3

```
Met His Arg Gln Pro Ser Pro His Ala Phe Ser Ser Gly Ser Trp
 1               5                  10                  15

Ala Glu Gln Gly Ala Gly Gly Tyr Arg His Gly Arg Asp Gly Ala Thr
                20                  25                  30

Phe Leu Leu Pro Glu Leu Leu Gln Arg Ser Pro Asn Pro Ser Ser Lys
        35                  40                  45

Ser Ser Ala Ala Thr Phe Val Pro Pro Leu Ala Ala His Gly
    50                  55                  60

Gly Gly Val Ala Ala Pro Phe Gly Met Ala Pro Leu Gly Val Ala Ala
65                  70                  75                  80

Ala Asp Glu Ala Arg Phe Cys Met Thr Pro Trp Ser Ala Ala His
                85                  90                  95

Phe Glu Asn Trp Gly Asp Ser Gly Ile Val Val Thr Ser Pro Leu Ala
            100                 105                 110

Glu Thr Ala Ser Thr Asp Val Asp Met Gly Gly Gly Ala Met Ala
        115                 120                 125

Gln Ser Val Asp Gly His Asp Asn Ser Leu Pro Ala Cys Lys Val Glu
    130                 135                 140

Pro Arg Asp His Lys Ala Gln Arg Arg Leu Ala Gln Asn Arg Glu Ala
145                 150                 155                 160

Ala Arg Lys Ser Arg Met Arg Lys Lys Ala Tyr Ile Val Glu Leu Glu
                165                 170                 175

Asn Ser Arg Ser Lys Leu Ser His Leu Glu Gln Glu Leu Gln Arg Ala
            180                 185                 190

Arg Gln Gln Gly Met Phe Ile Ala Ser Gly Arg Ser Gly Asp His Gly
```

```
                195                 200                 205
Cys Ser Thr Gly Gly Ala Leu Ala Phe Asp Leu Glu Tyr Ala Arg Trp
    210                 215                 220

Leu Asp Glu His Gln His His Met Asn Asp Leu Arg Val Ala Leu Ser
225                 230                 235                 240

Ala Gln Ile Gly Asp Asp Leu Gly Val Leu Val Asp Gly Ala Met
                245                 250                 255

Leu His Tyr Asp Gln Met Phe Arg Leu Lys Gly Val Ala Thr Arg Thr
                260                 265                 270

Asp Val Phe His Val Leu Ser Gly Met Trp Met Ser Pro Ala Glu Arg
                275                 280                 285

Phe Phe Met Trp Leu Gly Gly Phe Arg Ser Ser Glu Leu Leu Lys Val
    290                 295                 300

Leu Ala Arg His Val Glu Pro Leu Thr Glu Gln Gln Leu Val Gly Ile
305                 310                 315                 320

Cys Gly Leu Gln Gln Ser Leu Gln Gln Ala Glu Asp Ala Leu Ser Gln
                325                 330                 335

Gly Met Glu Ala Leu Gln Gln Ala Leu Gly Asp Thr Leu Ala Ala Ala
                340                 345                 350

Ala Thr Pro Cys Ala Ala Asp Ser Val Thr Asn Tyr Met Gly Gln Met
                355                 360                 365

Ala Val Ala Met Ser Lys Leu Ala Thr Val Glu Asn Phe Leu Arg Gln
    370                 375                 380

Ala Asp Leu Leu Arg Gln Gln Thr Leu Lys Gln Val Arg Arg Ile Leu
385                 390                 395                 400

Thr Thr Arg Gln Ala Ala Arg Ala Leu Leu Val Ile Ser Asp Tyr Phe
                405                 410                 415

Ser Arg Leu Arg Ala Leu Ser Ser Leu Trp Leu Thr Arg Pro Thr Asp
                420                 425                 430

<210> SEQ ID NO 4
<211> LENGTH: 2766
<212> TYPE: DNA
<213> ORGANISM: Zea mays

<400> SEQUENCE: 4
tcttcatcaa atttgcgcgg cgtctgcgtt ccctgcttcc cattcgaaaa caaaagcaaa      60
aggtgcgcat tcacggtgtc gccctcgtct ctactcgtgt ctcgtcttgg gtagcgtacg     120
caccttagct cgcaaccatc catccatcca cggggctcgg gcgcagcagc ctcccccgtc     180
gtcgtcttcg tcgtcgcctt gccgccgctc tgatccgtgc ccgatgcatc gtcagccatc     240
tcctcacgcc ttcaggtagt aaaagtatac taagccgcag ggcaccacaa cgcaacacgt     300
ggtgcctgcc tgcctccttc cttgttcgct tgcggcgcg agcgttttgt ctgttgttgt     360
ctcccttggg accggcgcgt ccggctggct cactaccact aacgtgttgt tgcctgcctt     420
gtgcggcgcc cgtggttcgc attgcgtttg cagcagcagc ggcagctggg cggagcaggg     480
cgcgggcggg taccgccacg gcagggacgg cgccaccttc ctcctccccg agctcctcca     540
gcgcagtaat aacgccgccc tgccccttgt ttatccgcct gcctgcgtat tttgtttcct     600 ttcttttttct tcttgttgga tttctcatgg ctgttggttg cacgcgcgcg catcgcgggg     660
gctaatgtga aggccccaac cccagctcca gtcctccag gccgccacc ttcgtgccgc      720 cgctcgccgc cgcggtgagt tcactgactg agaatgagat acggtcgtt ctccgccgcg      780 gcttcttcac tttgagcgtg aatgacatgg aggctctctc tggcgtcttt ttgtctgcag     840
```

```
catggaggag gagtagcggc cccgtttggc atggcgccgc tgggagtggc ggcggcggac      900
gaagcccggt tctgcatgac gccgtggtca gcggcggcgc acttcgagaa ctggggcgac      960
tccggcatcg tcgtcaccag cccgctcgcc gagacggcct ccaccgacgt cgacatggtc     1020
tgctcctcaa tactcagctt ccatccatct tcatccgcat gcacagtata tatgcctgcc     1080
atgaactccg cctggagtat atgtatatgc cgtgacgtgt gactccaccg ccgtcgtcgt     1140
agggtggagg tggagccatg gcgcagagcg tcgacggaca tgacaactca ttgccggcgt     1200
gcaaggtgga gcccagggat cacaaggtgc gctatgccat gtcacgtgaa cacgtcgtcg     1260
tggtcccaaa aaggaactag aagagcagca gatgtgattg tggttttgt gctgtgtcat      1320
ggcaggcgca gaggaggctt gcgcaaaacc gcgaggcggc ccggaaaagc cggatgagga     1380
agaaggtgat ccccttccc ctcacgggaa gcttctgtac attatgctat gcttgcaagt      1440
tgcattccat cctgtcttct tcttgctcag tacccccctg tttatttacc ctgacgggag     1500
gcttactgag ttttgtctac agttttactg taccatgctg tcactgtttc cacttgcaag     1560
atcgctgaag cactgtgcaa attcgctctg taggcgtaca ttgtggagct ggaaaacagc     1620
cggtccaagc tgtcccatct tgagcaggag cttcaaaggg caaggcagca ggtgaactcc     1680
tgatctgttt tcctctgaag aacgaaacga tccatactac ttcgacgctg attgtctatg     1740
ggctgtaaat acaggggatg ttcattgcaa gtggacgctc cggagatcat ggatgctcca     1800
ctggaggcag atgatctttt tttcttctct tttacattgc tcagctcttg ttctctgaat     1860
tctgatcctg tgcaatgtaa agcctaacct gtgtccttgc aggtgcgttg gcgttcgacc     1920
tggagtacgc gcggtggctg gacgagcacc agcaccacat gaacgacctc cgggtggccc     1980
tgagcgcgta gatcggcgac gacgacctgg gcgtgctggt ggacggcgcg atgctgcact     2040
acgaccagat gttccggctc aagggcgtgg ccacgaggac ggacgtgttc cacgtgctgt     2100
cgggcatgtg gatgagcccc gcggagcggt tcttcatgtg gctgggcggg ttccggtcgt     2160
cggagctgct caaggtgctg gcgcggcacg tggagccgct gacggagcag cagctggtgg     2220
gcatctgcgg cctgcagcag tcgctgcagc aggccgagga cgcgctgtcg caggggatgg     2280
aggccctgca gcaggccctc ggggacacgc tcgccgccgc cgccacgccg tgcgccgccg     2340
acagcgtcac caactacatg ggccagatgg ccgtcgccat gagcaagctc gccaccgtgg     2400
agaacttcct ccgccaggcg gacctgctgc ggcagcagac gctgaagcag gtgcgccgga     2460
tcctgaccac gcgccaagcc gcgcgcgcgc tgctcgtcat cagtgactac ttctcgcggc     2520
tccgtgcgct cagctccctg tggctgacgc ggccgacgga ttgattcggc gtaggcacac     2580
ggacgggagc tgtcgttggt tggttgcgct gagactgtaa tctgtatccg ttgtgagatg     2640
gggtgaccat gcggattcat caggcagaaa cggcgaatgt gtctagcttt agttttggct     2700
accattcagc ttcatcagtg aggctagagt agagcgattt cggtgcgcat gtccaggctt     2760
ttgctc                                                                2766

<210> SEQ ID NO 5
<211> LENGTH: 726
<212> TYPE: DNA
<213> ORGANISM: Zea mays

<400> SEQUENCE: 5
atgcatcgtc agccatctcc tcacgccttc agcagcagcg gcagctgggc ggagcagggc       60
gcgggcgggt accgccacgg cagggacggc gccaccttcc tcctcccga gctcctccag      120
```

-continued

```
cgcagcccca accccagctc caagtcctcc agcgccgcca ccttcgtgcc gccgctcgcc    180
gccgcgcatg gaggaggagt agcggccccg tttggcatgg cgccgctggg agtggcggcg    240
gcggacgaag cccggttctg catgacgccg tggtcagcgg cggcgcactt cgagaactgg    300
ggcgactccg gcatcgtcgt caccagcccg ctcgccgaga cggcctccac cgacgtcgac    360
atgggtggag gtggagccat ggcgcagagc gtcgacggac atgacaactc attgccggcg    420
tgcaaggtgg agcccaggga tcacaaggcg cagaggaggc ttgcgcaaaa ccgcgaggcg    480
gcccggaaaa gccggatgag gaagaaggcg tacattgtgg agctggaaaa cagccggtcc    540
aagctgtccc atcttgagca ggagcttcaa agggcaaggc agcaggggat gttcattgca    600
agtggacgct ccggagatca tggatgctcc actggaggtg cgttggcgtt cgacctggag    660
tacgcgcggt ggctggacga gcaccagcac cacatgaacg acctccgggt ggccctgagc    720
gcgtag                                                               726
```

<210> SEQ ID NO 6
<211> LENGTH: 241
<212> TYPE: PRT
<213> ORGANISM: Zea mays

<400> SEQUENCE: 6

```
Met His Arg Gln Pro Ser Pro His Ala Phe Ser Ser Ser Gly Ser Trp
1               5                   10                  15

Ala Glu Gln Gly Ala Gly Gly Tyr Arg His Gly Arg Asp Gly Ala Thr
            20                  25                  30

Phe Leu Leu Pro Glu Leu Leu Gln Arg Ser Pro Asn Pro Ser Ser Lys
        35                  40                  45

Ser Ser Ala Ala Thr Phe Val Pro Pro Leu Ala Ala Ala His Gly
    50                  55                  60

Gly Gly Val Ala Ala Pro Phe Gly Met Ala Pro Leu Gly Val Ala Ala
65                  70                  75                  80

Ala Asp Glu Ala Arg Phe Cys Met Thr Pro Trp Ser Ala Ala His
                85                  90                  95

Phe Glu Asn Trp Gly Asp Ser Gly Ile Val Val Thr Ser Pro Leu Ala
            100                 105                 110

Glu Thr Ala Ser Thr Asp Val Asp Met Gly Gly Gly Ala Met Ala
        115                 120                 125

Gln Ser Val Asp Gly His Asp Asn Ser Leu Pro Ala Cys Lys Val Glu
    130                 135                 140

Pro Arg Asp His Lys Ala Gln Arg Arg Leu Ala Gln Asn Arg Glu Ala
145                 150                 155                 160

Ala Arg Lys Ser Arg Met Arg Lys Lys Ala Tyr Ile Val Glu Leu Glu
                165                 170                 175

Asn Ser Arg Ser Lys Leu Ser His Leu Glu Gln Glu Leu Gln Arg Ala
            180                 185                 190

Arg Gln Gln Gly Met Phe Ile Ala Ser Gly Arg Ser Gly Asp His Gly
        195                 200                 205

Cys Ser Thr Gly Gly Ala Leu Ala Phe Asp Leu Glu Tyr Ala Arg Trp
    210                 215                 220

Leu Asp Glu His Gln His His Met Asn Asp Leu Arg Val Ala Leu Ser
225                 230                 235                 240

Ala
```

<210> SEQ ID NO 7

<211> LENGTH: 2766
<212> TYPE: DNA
<213> ORGANISM: Zea mays

<400> SEQUENCE: 7

| | | | | | |
|---|---|---|---|---|---|
| tcttcatcaa | atttgcgcgg | cgtctgcgtt | ccctgcttcc | cattcgaaaa | caaaagcaaa | 60 |
| aggtgcgcat | tcacggtgtc | gccctcgtct | ctactcgtgt | ctcgtcttgg | gtagcgtacg | 120 |
| caccttagct | cgcaaccatc | catccatcca | cggggctcgg | gcgcagcagc | ctcccccgtc | 180 |
| gtcgtcttcg | tcgtcgcctt | gccgccgctc | tgatccgtgc | ccgatgcatc | gtcagccatc | 240 |
| tcctcacgcc | ttcaggtagt | aaaagtatac | taagccgcag | ggcaccacaa | cgcaacacgt | 300 |
| ggtgcctgcc | tgcctccttc | cttgttcgct | ttgcggcgcg | agcgttttgt | ctgttgttgt | 360 |
| ctcccttggg | accggcgcgt | ccggctggct | cactaccact | aacgtgttgt | tgcctgcctt | 420 |
| gtgcggcgcc | cgtggttcgc | attgcgtttg | cagcagcagc | ggcagctggg | cggagcaggg | 480 |
| cgcgggcggg | taccgccacg | gcagggacgg | cgccaccttc | ctcctcccg | agctcctcca | 540 |
| gcgcagtaat | aacgccgccc | tgcccttgt | ttatccgcct | gcctgcgtat | tttgtttcct | 600 |
| ttcttttttct | tcttgttgga | tttctcatgg | ctgttggttg | cacgcgcgcg | catcgcgggg | 660 |
| gctaatgtga | aggccccaac | cccagctcca | agtcctccag | cgccgccacc | ttcgtgccgc | 720 |
| cgctcgccgc | cgcggtgagt | tcactgactg | agaatgagat | acggttcgtt | ctccgccgcg | 780 |
| gcttcttcac | tttgagcgtg | aatgacatgg | aggctctctc | tggcgtcttt | ttgtctgcag | 840 |
| catggaggag | gagtagcggc | cccgtttggc | atggcgccgc | tgggagtggc | ggcggcggac | 900 |
| gaagcccggt | tctgcatgac | gccgtggtca | gcggcggcgc | acttcgagaa | ctggggcgac | 960 |
| tccggcatcg | tcgtcaccag | cccgctcgcc | gagacggcct | ccaccgacgt | cgacatggtc | 1020 |
| tgctcctcaa | tactcagctt | ccatccatct | tcatccgcat | gcacagtata | tatgcctgcc | 1080 |
| atgaactccg | cctggagtat | atgtatatgc | cgtgacgtgt | gactccaccg | ccgtcgtcgt | 1140 |
| agggtggagg | tggagccatg | gcgcagagcg | tcgacggaca | tgacaactca | ttgccggcgt | 1200 |
| gcaaggtgga | gcccagggat | cacaaggtgc | gctatgccat | gtcacgtgaa | cacgtcgtcg | 1260 |
| tggtcccaaa | aaggaactag | aagagcagca | gatgtgattg | tggttttttgt | gctgtgtcat | 1320 |
| ggcaggcgca | gaggaggctt | gcgcaaaacc | gcgaggcggc | ccggaaaagc | cggatgagga | 1380 |
| agaaggtgat | ccccttccc | ctcacgggaa | gcttctgtac | attatgctat | gcttgcaagt | 1440 |
| tgcattccat | cctgtcttct | tcttgctcag | tacccccctg | tttatttacc | ctgacgggag | 1500 |
| gcttactgag | ttttgtctac | agttttactg | taccatgctg | tcactgtttc | cacttgcaag | 1560 |
| atcgctgaag | cactgtgcaa | attcgctctg | taggcgtaca | ttgtggagct | ggaaaacagc | 1620 |
| cggtccaagc | tgtcccatct | tgagcaggag | cttcaaaggg | caaggcagca | ggtgaactcc | 1680 |
| tgatctgttt | tcctctgaag | aacgaaacga | tccatactac | ttcgacgctg | attgtctatg | 1740 |
| ggctgtaaat | acaggggatg | ttcattgcaa | gtggacgctc | cggagatcat | ggatgctcca | 1800 |
| ctggaggcag | atgatctttt | tttcttctct | tttacattgc | tcagctcttg | ttctctgaat | 1860 |
| tctgatcctg | tgcaatgtaa | agcctaacct | gtgtccttgc | aggtgcgttg | gcgttcgacc | 1920 |
| tggagtacgc | gcgtggctg | gacgagcacc | agcaccacat | gaacgacctc | cgggtggccc | 1980 |
| tgagcgcgca | gatcggcgac | gacgacctgg | gcgtgctggt | ggacggcgcg | atgctgcact | 2040 |
| acgaccagat | gttccggctc | aagggcgtgg | ccacgaggac | ggacgtgttc | cacgtgctgt | 2100 |
| cgggcatgta | gatgagcccc | gcggagcggt | tcttcatgtg | gctgggcggg | ttccggtcgt | 2160 |
| cggagctgct | caaggtgctg | gcgcggcacg | tggagccgct | gacggagcag | cagctggtgg | 2220 |

```
gcatctgcgg cctgcagcag tcgctgcagc aggccgagga cgcgctgtcg caggggatgg    2280
aggccctgca gcaggccctc ggggacacgc tcgccgccgc cgccacgccg tgcgccgccg    2340
acagcgtcac caactacatg ggccagatgg ccgtcgccat gagcaagctc gccaccgtgg    2400
agaacttcct ccgccaggcg gacctgctgc ggcagcagac gctgaagcag gtgcgccgga    2460
tcctgaccac gcgccaagcc gcgcgcgcgc tgctcgtcat cagtgactac ttctcgcggc    2520
tccgtgcgct cagctccctg tggctgacgc ggccgacgga ttgattcggc gtaggcacac    2580
ggacgggagc tgtcgttggt tggttgcgct gagactgtaa tctgtatccg ttgtgagatg    2640
gggtgaccat gcggattcat caggcagaaa cggcgaatgt gtctagcttt agttttggct    2700
accattcagc ttcatcagtg aggctagagt agagcgattt cggtgcgcat gtccaggctt    2760
ttgctc                                                              2766

<210> SEQ ID NO 8
<211> LENGTH: 846
<212> TYPE: DNA
<213> ORGANISM: Zea mays

<400> SEQUENCE: 8
atgcatcgtc agccatctcc tcacgccttc agcagcagcg gcagctgggc ggagcagggc      60
gcgggcgggt accgccacgg cagggacggc gccaccttcc tcctcccga gctcctccag     120 cgcagcccca accccagctc caagtcctcc agcgccgcca ccttcgtgcc gccgctcgcc     180
gccgcgcatg gaggaggagt agcggccccg tttggcatgg cgccgctggg agtggcggcg     240
gcggacgaag cccggttctg catgacgccg tggtcagcgg cggcgcactt cgagaactgg     300
ggcgactccg gcatcgtcgt caccagcccg ctcgccgaga cggcctccac cgacgtcgac     360
atgggtggag gtggagccat ggcgcagagc gtcgacggac atgacaactc attgccggcg     420
tgcaaggtgg agcccaggga tcacaaggcg cagaggaggc ttgcgcaaaa ccgcgaggcg     480
gcccggaaaa gccggatgag gaagaaggcg tacattgtgg agctggaaaa cagccggtcc     540
aagctgtccc atcttgagca ggagcttcaa agggcaaggc agcaggggat gttcattgca     600
agtggacgct ccggagatca tggatgctcc actggaggtg cgttggcgtt cgacctggag     660
tacgcgcggt ggctggacga gcaccagcac cacatgaacg acctccgggt ggccctgagc     720
gcgcagatcg cgacgacga cctgggcgtg ctggtgacg cgcgatgct gcactacgac      780 cagatgttcc ggctcaaggg cgtggccacg aggacggacg tgttccacgt gctgtcgggc     840
atgtag                                                              846

<210> SEQ ID NO 9
<211> LENGTH: 281
<212> TYPE: PRT
<213> ORGANISM: Zea mays

<400> SEQUENCE: 9

Met His Arg Gln Pro Ser Pro His Ala Phe Ser Ser Ser Gly Ser Trp
1               5                   10                  15

Ala Glu Gln Gly Ala Gly Gly Tyr Arg His Gly Arg Asp Gly Ala Thr
            20                  25                  30

Phe Leu Leu Pro Glu Leu Leu Gln Arg Ser Pro Asn Pro Ser Ser Lys
        35                  40                  45

Ser Ser Ser Ala Ala Thr Phe Val Pro Pro Leu Ala Ala Ala His Gly
    50                  55                  60
```

Gly Gly Val Ala Ala Pro Phe Gly Met Ala Pro Leu Gly Val Ala Ala
 65                  70                  75                  80

Ala Asp Glu Ala Arg Phe Cys Met Thr Pro Trp Ser Ala Ala His
             85                  90                  95

Phe Glu Asn Trp Gly Asp Ser Gly Ile Val Val Thr Ser Pro Leu Ala
            100                 105                 110

Glu Thr Ala Ser Thr Asp Val Asp Met Gly Gly Gly Ala Met Ala
        115                 120                 125

Gln Ser Val Asp Gly His Asp Asn Ser Leu Pro Ala Cys Lys Val Glu
130                 135                 140

Pro Arg Asp His Lys Ala Gln Arg Arg Leu Ala Gln Asn Arg Glu Ala
145                 150                 155                 160

Ala Arg Lys Ser Arg Met Arg Lys Lys Ala Tyr Ile Val Glu Leu Glu
                165                 170                 175

Asn Ser Arg Ser Lys Leu Ser His Leu Glu Gln Glu Leu Gln Arg Ala
            180                 185                 190

Arg Gln Gln Gly Met Phe Ile Ala Ser Arg Ser Gly Asp His Gly
        195                 200                 205

Cys Ser Thr Gly Gly Ala Leu Ala Phe Asp Leu Glu Tyr Ala Arg Trp
210                 215                 220

Leu Asp Glu His Gln His His Met Asn Asp Leu Arg Val Ala Leu Ser
225                 230                 235                 240

Ala Gln Ile Gly Asp Asp Leu Gly Val Leu Val Asp Gly Ala Met
                245                 250                 255

Leu His Tyr Asp Gln Met Phe Arg Leu Lys Gly Val Ala Thr Arg Thr
            260                 265                 270

Asp Val Phe His Val Leu Ser Gly Met
        275                 280

<210> SEQ ID NO 10
<211> LENGTH: 2968
<212> TYPE: DNA
<213> ORGANISM: Arabidopsis thaliana

<400> SEQUENCE: 10
tctttctctc tctcacacac aatatagtaa tttcgtattt attaatgatg aatcctccag      60
ccgtactgat tcgccatctt ttcacctctt taatgaattc tctcctcact ccctccttcc     120
cttttaactt cactttcttc ttctgataac ccaactcctt aagaaagctc acttcttttt     180
cccctgattc cctttgtgtc atcatctttc atcatcttct tcttctaaga atcaacaaca     240
atgcagagca gcttcaaaac cgttcctttc actcctgatt tctactctca gtcttcttac     300
ttcttcaggt aacaacactt ctccttctct cttttctct tcttaaaaag cttcaacaac     360
aaaaaaaaaa accaatcttt tttgttctta atggaaaaac agaggagata gttgtcttga     420
ggagtttcat caaccagtca atggttttca ccatgaagaa gctatcgatt taagtccaag     480
ttagcttctt tttctcttcc tttttcctta caagtgcaaa aaggtttaag ctttgttgaa     540
agaatctcaa gtaggttcca ttttctgatt tcctgcagat gtcactattg cttcagctaa     600
cttacactac acgacgtttg atacggtaaa aagttcacca aacccaaatt tttaaaatag     660
aaaaaagttt ccgttttttt agctcagact ttctatgtat gtatgtatac tctgtttttt     720
aggttatgga ttgtggtggt ggtggtggtg gtggcttgag ggagagactt gaaggaggag     780
aagaggagtg tttggacaca gggcaactag tgtaccagaa agggacaaga ttagtaggag     840
gaggagtagg agaagtgaac agcagttggt gtgattcggt ttcagctatg gctgataaca     900

| gtcaacatac tgacacttcc acagatattg atactgatga caagactcag gttttgttcc | 960 |
| tttgtcttct tcaataacca atctctctgt ctgtcacaac caaaaaaaaa gataaaaaga | 1020 |
| ttctgtctttt tttttcttcc atttctgtttt tgtttcttct acacttgttg gagttttgtt | 1080 |
| ttgtcccttt tgtttttttt tataatttct cattgatatg tcaccttggt attcgatcaa | 1140 |
| tattgtttgc tcagattatg tctgtttcaa taagagcttg tctgttttgt tttttggttt | 1200 |
| aatgggacac aacatggatg attggtttgt tgaatttact actaaaattt acaagtttct | 1260 |
| tccttttttat ggttatgaac ttatgatatg aaaaacgtta cttggccgtg ttgatgttgc | 1320 |
| ttgtaaagtt tgttgtttca ttatttatag ttgcattgat gtatattgat tggtttgtgt | 1380 |
| tatatagttg aatggaggtc atcaagggat gctattggct acaaattgtt cagatcaatc | 1440 |
| caatgtgaaa tctagtgatc aaagggtaga tcttctgatt ttaaccattt gagttttgga | 1500 |
| tacgttggtt tatgtgtgaa tgaactttg acatttttga attcttggca gacacttcgt | 1560 |
| cgacttgctc agaaccggga ggctgctagg aaaagtcggt tgaggaaaaa ggtatagtag | 1620 |
| ctgattcaac tgtgtttttc atcgtccatt atctttgtat ttacattgtc ttttaatagg | 1680 |
| catatgttca gcaacttgag aatagtcgaa tcaggcttgc acagctagag gaagagctca | 1740 |
| aaagagctcg ccaacaggtc tgattaacac tgttgtcttc tttaatttgc atgttctact | 1800 |
| aaattgtatt aaagggcttc ttttgtatgc agggatcttt ggttgaaaga ggagtttcag | 1860 |
| cggatcacac gcatttggca gccggaaatg gtaaagactt tcagaatctc acataacact | 1920 |
| tcttgactct ttgtgatctt ttactaagaa tgaagttggt tttgatgttg taggtgtctt | 1980 |
| ttcatttgaa ttggaatata cacgttggaa ggaagaacat caaagaatga tcaacgactt | 2040 |
| aagatcgggt gtgaattcgc agttaggtga caacgatcta cgcgttctag tggatgctgt | 2100 |
| gatgagtcac tatgatgaaa tattcaggct aaagggaatt ggtactaaag ttgacgtctt | 2160 |
| tcatatgctc tcaggcatgt ggaagacacc tgccgagaga ttttcatgt ggttaggtgg | 2220 |
| atttagatca tcagagttac ttaaggtaaa agaaagggtt caaaacattt tcacaatcat | 2280 |
| tggttttgat ttttttttct cataattggt aactatgttg ttagatattg gggaaccatg | 2340 |
| tggatccatt gacggaccag cagttgatag gcatttgcaa ccttcagcaa tcgtctcaac | 2400 |
| aagcagagga tgcattgtca caaggcatgg aagctctaca acaatcactt ctcgagacgc | 2460 |
| tttcttctgc ttcaatgggt ccaaactctt cagcaaatgt tgcagattat atgggtcata | 2520 |
| tggctatggc tatgggcaaa cttggcactc ttgaaaactt ccttcgccag gtaagaaaaa | 2580 |
| atgaacagaa tgtctcttgt caacaacaac atttgttatt acaaatcaaa gagcttaaag | 2640 |
| gttactatat ctttgcaggc tgatttattg aggcaacaaa ctctgcaaca gcttcacaga | 2700 |
| attctcacca cacgacaagc tgctcgcgcc ttttggtca tccacgatta tatttctcgg | 2760 |
| cttagagcac ttagctctct atggttagcc agacctagag actaaataaa aagcctgcat | 2820 |
| gagtcatgat gaccaaagga aaagcatagt tctggtctta ggttttcata tttacatatt | 2880 |
| tttaactaaa agacccataa cgctcttctc tttagtgtat tagatcatct gtttatttag | 2940 |
| ttggtagtga acgttaccat tcagaatc | 2968 |

<210> SEQ ID NO 11
<211> LENGTH: 1762
<212> TYPE: DNA
<213> ORGANISM: Arabidopsis thaliana

<400> SEQUENCE: 11

-continued

| | |
|---|---|
| tctttctctc tctcacacac aatatagtaa tttcgtattt attaatgatg aatcctccag | 60 |
| ccgtactgat tcgccatctt ttcacctctt taatgaattc tctcctcact ccctccttcc | 120 |
| cttttaactt cactttcttc ttctgataac ccaactcctt aagaaagctc acttctttt | 180 |
| cccctgattc cctttgtgtc atcatctttc atcatcttct tcttctaaga atcaacaaca | 240 |
| atgcagagca gcttcaaaac cgttcctttc actcctgatt tctactctca gtcttcttac | 300 |
| ttcttcagag gagatagttg tcttgaggag tttcatcaac cagtcaatgg ttttcaccat | 360 |
| gaagaagcta tcgatttaag tccaaatgtc actattgctt cagctaactt acactacacg | 420 |
| acgtttgata cggttatgga ttgtggtggt ggtggtggtg gtggcttgag ggagagactt | 480 |
| gaaggaggag aagaggagtg tttggacaca gggcaactag tgtaccagaa agggacaaga | 540 |
| ttagtaggag gaggagtagg agaagtgaac agcagttggt gtgattcggt ttcagctatg | 600 |
| gctgataaca gtcaacatac tgacacttcc acagatattg atactgatga caagactcag | 660 |
| ttgaatggag gtcatcaagg gatgctattg gctacaaatt gttcagatca atccaatgtg | 720 |
| aaatctagtg atcaaaggac acttcgtcga cttgctcaga accgggaggc tgctaggaaa | 780 |
| agtcggttga ggaaaaaggc atatgttcag caacttgaga atagtcgaat caggcttgca | 840 |
| cagctagagg aagagctcaa aagagctcgc caacagggat ctttggttga agaggagtt | 900 |
| tcagcggatc acacgcattt ggcagccgga aatggtgtct tttcatttga attggaatat | 960 |
| acacgttgga aggaagaaca tcaaagaatg atcaacgact aagatcgggg tgtgaattcg | 1020 |
| cagttaggtg acaacgatct acgcgttcta gtggatgctg tgatgagtca ctatgatgaa | 1080 |
| atattcaggc taaagggaat tggtactaaa gttgacgtct ttcatatgct ctcaggcatg | 1140 |
| tggaagacac ctgccgagag attttcatg tggttaggtg gatttagatc atcagagtta | 1200 |
| cttaagatat tggggaacca tgtggatcca ttgacggacc agcagttgat aggcatttgc | 1260 |
| aaccttcagc aatcgtctca acaagcagag gatgcattgt cacaaggcat ggaagctcta | 1320 |
| caacaatcac ttctcgagac gctttcttct gcttcaatgg gtccaaactc ttcagcaaat | 1380 |
| gttgcagatt atatgggtca tatggctatg gctatgggca aacttggcac tcttgaaaac | 1440 |
| ttccttcgcc aggctgattt attgaggcaa caaactctgc aacagcttca cagaattctc | 1500 |
| accacacgac aagctgctcg cgccttttg gtcatccacg attatatttc tcggcttaga | 1560 |
| gcacttagct ctctatggtt agccagacct agagactaaa taaaaagcct gcatgagtca | 1620 |
| tgatgaccaa aggaaaagca tagttctggt cttaggtttt catatttaca tatttttaac | 1680 |
| taaaagaccc ataacgctct tctctttagt gtattagatc atctgtttat ttagttggta | 1740 |
| gtgaacgtta ccattcagaa tc | 1762 |

<210> SEQ ID NO 12
<211> LENGTH: 452
<212> TYPE: PRT
<213> ORGANISM: Arabidopsis thaliana

<400> SEQUENCE: 12

Met Gln Ser Ser Phe Lys Thr Val Pro Phe Thr Pro Asp Phe Tyr Ser
1               5                   10                  15

Gln Ser Ser Tyr Phe Phe Arg Gly Asp Ser Cys Leu Glu Glu Phe His
            20                  25                  30

Gln Pro Val Asn Gly Phe His His Glu Glu Ala Ile Asp Leu Ser Pro
        35                  40                  45

Asn Val Thr Ile Ala Ser Ala Asn Leu His Tyr Thr Thr Phe Asp Thr
    50                  55                  60

Val Met Asp Cys Gly Gly Gly Gly Gly Leu Arg Glu Arg Leu
65                  70                  75                  80

Glu Gly Gly Glu Glu Glu Cys Leu Asp Thr Gly Gln Leu Val Tyr Gln
                85                  90                  95

Lys Gly Thr Arg Leu Val Gly Gly Val Gly Glu Val Asn Ser Ser
            100                 105                 110

Trp Cys Asp Ser Val Ser Ala Met Ala Asp Asn Ser Gln His Thr Asp
        115                 120                 125

Thr Ser Thr Asp Ile Asp Thr Asp Lys Thr Gln Leu Asn Gly Gly
130                 135                 140

His Gln Gly Met Leu Leu Ala Thr Asn Cys Ser Asp Gln Ser Asn Val
145                 150                 155                 160

Lys Ser Ser Asp Gln Arg Thr Leu Arg Arg Leu Ala Gln Asn Arg Glu
                165                 170                 175

Ala Ala Arg Lys Ser Arg Leu Arg Lys Lys Ala Tyr Val Gln Gln Leu
            180                 185                 190

Glu Asn Ser Arg Ile Arg Leu Ala Gln Leu Glu Glu Leu Lys Arg
        195                 200                 205

Ala Arg Gln Gln Gly Ser Leu Val Glu Arg Gly Val Ser Ala Asp His
210                 215                 220

Thr His Leu Ala Ala Gly Asn Gly Val Phe Ser Phe Glu Leu Glu Tyr
225                 230                 235                 240

Thr Arg Trp Lys Glu Glu His Gln Arg Met Ile Asn Asp Leu Arg Ser
                245                 250                 255

Gly Val Asn Ser Gln Leu Gly Asp Asn Asp Leu Arg Val Leu Val Asp
            260                 265                 270

Ala Val Met Ser His Tyr Asp Glu Ile Phe Arg Leu Lys Gly Ile Gly
        275                 280                 285

Thr Lys Val Asp Val Phe His Met Leu Ser Gly Met Trp Lys Thr Pro
290                 295                 300

Ala Glu Arg Phe Phe Met Trp Leu Gly Gly Phe Arg Ser Ser Glu Leu
305                 310                 315                 320

Leu Lys Ile Leu Gly Asn His Val Asp Pro Leu Thr Asp Gln Gln Leu
                325                 330                 335

Ile Gly Ile Cys Asn Leu Gln Gln Ser Ser Gln Gln Ala Glu Asp Ala
            340                 345                 350

Leu Ser Gln Gly Met Glu Ala Leu Gln Gln Ser Leu Leu Glu Thr Leu
        355                 360                 365

Ser Ser Ala Ser Met Gly Pro Asn Ser Ser Ala Asn Val Ala Asp Tyr
370                 375                 380

Met Gly His Met Ala Met Ala Met Gly Lys Leu Gly Thr Leu Glu Asn
385                 390                 395                 400

Phe Leu Arg Gln Ala Asp Leu Leu Arg Gln Gln Thr Leu Gln Gln Leu
                405                 410                 415

His Arg Ile Leu Thr Thr Arg Gln Ala Ala Arg Ala Phe Leu Val Ile
            420                 425                 430

His Asp Tyr Ile Ser Arg Leu Arg Ala Leu Ser Ser Leu Trp Leu Ala
        435                 440                 445

Arg Pro Arg Asp
    450

<210> SEQ ID NO 13
<211> LENGTH: 951

-continued

```
<212> TYPE: DNA
<213> ORGANISM: Sorghum bicolor

<400> SEQUENCE: 13
ggtgttgcca tcacgcggag cgtcgacgga cacgagaact cattgccggt gtgcaaggta      60
gaatcgaggg atcacaaggc gcagaggagg cttgcgcaaa accgagaggc cgccaggaaa     120
agccggatga ggaagaaggc atacattgtg gagctggaga cagccggtc caagctggct      180
cagcttgagc aggagcttca aagggcaagg cagcagggga tgttcattgc aagtggacgg     240
tccggtgatc atggaggctc cactggaggc gcgctggcgt cgatctgga gtacgcccgg      300
tggctggacg agcaccagca ccacatgaac gacctccgtg tggccctgag cgcgcagatc     360
ggcgacgacg acctgggcgt gctggtggac ggcgtgatgc tgcactacga cgagatgttc     420
cggctcaagg gcgtggccac ccggacggac gtgttccacg tgctgtcggg catgtggatg     480
agccccgcgg agcggttctt catgtggctg ggcgggttcc ggtcgtcgga gctgctcaag     540
gtggtggcgc ggcaggtgga gccgcagctg acggagcagc agctggtggg catctgcagc     600
ctgcagcagt cgctgcagca ggcggaggac gcgctgtcgc aggggatgga ggccctgcag     660
cagggcctcg gggacacgct cgccgccgcc gccccggcgg cgcccggacc gtccgcgtcc     720
gccgccgaca gcgtcaccaa ctacatgggc cagatggccg tcgccatgag caagctcgcc     780
accgtggaga acttcctccg gcaggcggac ctgctgcggc agcagacgct gaagcaggtg     840
caccggatcc tgaccacccg ccaggccgcg cgcgcgctgc tcgtcgtcag cgactacttc     900
tcgcggctcc gagcgctcag ctccctgtgg ctgacgcgcc ccacggattg a              951

<210> SEQ ID NO 14
<211> LENGTH: 316
<212> TYPE: PRT
<213> ORGANISM: Sorghum bicolor

<400> SEQUENCE: 14

Gly Val Ala Ile Thr Arg Ser Val Asp Gly His Glu Asn Ser Leu Pro
1               5                   10                  15

Val Cys Lys Val Glu Ser Arg Asp His Lys Ala Gln Arg Arg Leu Ala
            20                  25                  30

Gln Asn Arg Glu Ala Ala Arg Lys Ser Arg Met Arg Lys Lys Ala Tyr
        35                  40                  45

Ile Val Glu Leu Glu Asn Ser Arg Ser Lys Leu Ala Gln Leu Glu Gln
    50                  55                  60

Glu Leu Gln Arg Ala Arg Gln Gln Gly Met Phe Ile Ala Ser Gly Arg
65                  70                  75                  80

Ser Gly Asp His Gly Gly Ser Thr Gly Gly Ala Leu Ala Phe Asp Leu
                85                  90                  95

Glu Tyr Ala Arg Trp Leu Asp Glu His Gln His His Met Asn Asp Leu
            100                 105                 110

Arg Val Ala Leu Ser Ala Gln Ile Gly Asp Asp Leu Gly Val Leu
        115                 120                 125

Val Asp Gly Val Met Leu His Tyr Asp Glu Met Phe Arg Leu Lys Gly
    130                 135                 140

Val Ala Thr Arg Thr Asp Val Phe His Val Leu Ser Gly Met Trp Met
145                 150                 155                 160

Ser Pro Ala Glu Arg Phe Phe Met Trp Leu Gly Gly Phe Arg Ser Ser
                165                 170                 175

Glu Leu Leu Lys Val Val Ala Arg Gln Val Glu Pro Gln Leu Thr Glu
```

```
                180                  185                  190
Gln Gln Leu Val Gly Ile Cys Ser Leu Gln Gln Ser Leu Gln Gln Ala
            195                  200                  205

Glu Asp Ala Leu Ser Gln Gly Met Glu Ala Leu Gln Gln Gly Leu Gly
210                  215                  220

Asp Thr Leu Ala Ala Ala Ala Pro Ala Ala Pro Gly Pro Ser Ala Ser
225                  230                  235                  240

Ala Ala Asp Ser Val Thr Asn Tyr Met Gly Gln Met Ala Val Ala Met
            245                  250                  255

Ser Lys Leu Ala Thr Val Glu Asn Phe Leu Arg Gln Ala Asp Leu Leu
            260                  265                  270

Arg Gln Gln Thr Leu Lys Gln Val His Arg Ile Leu Thr Thr Arg Gln
            275                  280                  285

Ala Ala Arg Ala Leu Leu Val Val Ser Asp Tyr Phe Ser Arg Leu Arg
            290                  295                  300

Ala Leu Ser Ser Leu Trp Leu Thr Arg Pro Thr Asp
305                  310                  315

<210> SEQ ID NO 15
<211> LENGTH: 1158
<212> TYPE: DNA
<213> ORGANISM: Oryza sativa

<400> SEQUENCE: 15
atggcggcgc accaggggat ggcggcggcg acggcggcgg accggttctg cctgccgagg      60
atggcggcgg cggcggcggc cgcctcgcag gtggagaact ggggcgactc cggcgtcatc     120
gtcagcagcc cgttcaccga cgacacctcc accgacctcg acgacagcgc cgacaagcac     180
cacctccacg ctctagtggg cggcggcgat ggcggcgacg acgccggcga gcagcgaggc     240
gcggattcct ccgccgtgtc caaggaaaga gaggggatc agaagatgca gcggaggctt      300
gcgcagaatc gcgaggcggc gcggaagagc cggatgagga agaaggcata cattcagcag     360
ttggagagca gcaggtccaa gctgatgcac cttgagcagg agctccaaag gcaagacag      420 cagggaatct tcattgcaac tggaggctcc ggcgatcacg gcactcgat cggaggaaat      480 ggtacgttgg cgttcgacct tgagtacgcg cggtggctgg acgagcacca gcggcacatc     540
aacgacctgc gggtggcgct gaacgcgcag atgagcgacg acgagctgtg cgagctcgtc     600
gacgccgtga tgatgcacta cgaccaggtg ttccgcctca agagcttcgc caccaagtcc     660
gacgtgttcc acgtcctctc cggcatgtgg atgagcccg ccgagcgctt cttcatgtgg      720
ctcggcggct tccgctcgtc ggagctcctc aaggttcttg ccagccatct tgagccgctg     780
acggatcagc agctgatggg catctgcaac ctgcagcagt cgtcgcagca ggccgaggac     840
gcgctgtcgc aggggatgga ggcgctgcag cagacgctgg gggacacgtt ggtgtcggcg     900
gccgccaccg tggtcagcgg cggcggcggc ccgacaacg tcaccaacta catgggacag      960
atggccatcg ccatggccaa gctcaccacg ctggagaact tcctccgtca ggctgatctg    1020
ctgaggcatc agacgctgca gcagatgcac cggatcctga ccacgaggca gcggcgcgg    1080 gcgctgctcg tcatcagcga ctacttctcg cggctccggg cgctgagctc gctgtggctg    1140
gcgcggccga gggactag                                                  1158

<210> SEQ ID NO 16
<211> LENGTH: 385
<212> TYPE: PRT
<213> ORGANISM: Oryza sativa
```

<400> SEQUENCE: 16

```
Met Ala Ala His Gln Gly Met Ala Ala Thr Ala Ala Asp Arg Phe
1               5                   10                  15

Cys Leu Pro Arg Met Ala Ala Ala Ala Ala Ser Gln Val Glu
            20                  25                  30

Asn Trp Gly Asp Ser Gly Val Ile Val Ser Ser Pro Phe Thr Asp Asp
                35                  40                  45

Thr Ser Thr Asp Leu Asp Asp Ser Ala Asp Lys His His Leu His Ala
    50                  55                  60

Leu Val Gly Gly Gly Asp Gly Asp Asp Ala Gly Glu Gln Arg Gly
65                  70                  75                  80

Ala Asp Ser Ser Ala Val Ser Lys Glu Arg Arg Gly Asp Gln Lys Met
                85                  90                  95

Gln Arg Arg Leu Ala Gln Asn Arg Glu Ala Ala Arg Lys Ser Arg Met
            100                 105                 110

Arg Lys Lys Ala Tyr Ile Gln Gln Leu Glu Ser Ser Arg Ser Lys Leu
        115                 120                 125

Met His Leu Glu Gln Glu Leu Gln Arg Ala Arg Gln Gln Gly Ile Phe
130                 135                 140

Ile Ala Thr Gly Gly Ser Gly Asp His Gly His Ser Ile Gly Gly Asn
145                 150                 155                 160

Gly Thr Leu Ala Phe Asp Leu Glu Tyr Ala Arg Trp Leu Asp Glu His
            165                 170                 175

Gln Arg His Ile Asn Asp Leu Arg Val Ala Leu Asn Ala Gln Met Ser
        180                 185                 190

Asp Asp Glu Leu Cys Glu Leu Val Asp Ala Val Met Met His Tyr Asp
            195                 200                 205

Gln Val Phe Arg Leu Lys Ser Phe Ala Thr Lys Ser Asp Val Phe His
        210                 215                 220

Val Leu Ser Gly Met Trp Met Ser Pro Ala Glu Arg Phe Phe Met Trp
225                 230                 235                 240

Leu Gly Gly Phe Arg Ser Ser Glu Leu Leu Lys Val Leu Ala Ser His
            245                 250                 255

Leu Glu Pro Leu Thr Asp Gln Gln Leu Met Gly Ile Cys Asn Leu Gln
        260                 265                 270

Gln Ser Ser Gln Gln Ala Glu Asp Ala Leu Ser Gln Gly Met Glu Ala
    275                 280                 285

Leu Gln Gln Thr Leu Gly Asp Thr Leu Val Ser Ala Ala Thr Val
    290                 295                 300

Val Ser Gly Gly Gly Ala Asp Asn Val Thr Asn Tyr Met Gly Gln
305                 310                 315                 320

Met Ala Ile Ala Met Ala Lys Leu Thr Thr Leu Glu Asn Phe Leu Arg
                325                 330                 335

Gln Ala Asp Leu Leu Arg His Gly Thr Leu Gln Met His Arg Ile
            340                 345                 350

Leu Thr Thr Arg Gln Ala Ala Arg Ala Leu Leu Val Ile Ser Asp Tyr
        355                 360                 365

Phe Ser Arg Leu Arg Ala Leu Ser Ser Leu Trp Leu Ala Arg Pro Arg
    370                 375                 380

Asp
385
```

<210> SEQ ID NO 17
<211> LENGTH: 1046
<212> TYPE: DNA
<213> ORGANISM: Zea mays

<400> SEQUENCE: 17

| | | | | | | |
|---|---|---|---|---|---|---|
| aaatttgatt | tagggggtgt | ttggttacat | tccgctaaaa | tttagcccct | gtcccatcga | 60 |
| atgtttaaac | ctccgttccg | ggtattaaat | gtagtcggat | tataaaacta | atttgtcagc | 120 |
| cgaagattaa | aagacaagac | gaatctagtc | cagttggttg | ggtttatatt | tcatactcct | 180 |
| aattaaaagt | caaacgcttg | atgtgaccca | ggctaaactt | tagcaggagc | aaccaaacat | 240 |
| ctcttagtag | tttagaaaag | cttgacttga | ttcaaatata | aactataagt | ttataataag | 300 |
| gaacgggaga | ttctcgtgac | cgtgtctcga | ctctctcacg | tgtcaccctg | ctccgccttt | 360 |
| tgtctctgct | cacgtaccag | tatcccagtc | aaagcgaggc | ggtaccccc | taaaacgtag | 420 |
| ggtcggacaa | caatatggct | accagccgaa | cactggcggt | ctggcgcaca | ccatcacatc | 480 |
| taaccattac | acagtacgca | cgctcccagg | ctcccgccag | tcacagaggc | ccactctccg | 540 |
| ggtcctcgag | cgaagcattt | gcattgccag | ccccgggact | cggccggcgc | acacgtaacc | 600 |
| acgcgcgcgc | tgctctgtgc | tctctgttgc | tgccaccctt | cctctgcgtt | cctccgactg | 660 |
| aatgatggac | tgaatgatgg | attggacgtg | cgcgctgatg | gatgagcagg | cctgacacca | 720 |
| aaattgacgc | gccccgatcg | tatctttcca | tcgatctctt | cctcctcgct | actctacgta | 780 |
| ctagtagact | agaaggctgt | gtagtagggc | tctgatccta | ttatcttcat | caaatttgcg | 840 |
| cggcgtctgc | gttccctgct | tcccattcga | aaacaaaagc | aaaaggtgcg | cattcacggt | 900 |
| gtcgccctcg | tctctactcg | tgtctcgtct | tgggtagcgt | acgcaccta | gctcgcaacc | 960 |
| atccatccat | ccacggggct | cgggcgcagc | agcctcccc | gtcgtcgtct | tcgtcgtcgc | 1020 |
| cttgccgccg | ctctgatccg | tgcccg | | | | 1046 |

<210> SEQ ID NO 18
<211> LENGTH: 3169
<212> TYPE: DNA
<213> ORGANISM: Artificial Sequence
<220> FEATURE:
<223> OTHER INFORMATION: YFP-FEA4 fusion protein-coding sequence

<400> SEQUENCE: 18

| | | | | | | |
|---|---|---|---|---|---|---|
| atgacaactt | tgtatacaaa | agttgcaggc | cggcctggag | gtggaggtgg | agctgtgagc | 60 |
| aagggcgagg | agctgttcac | cggggtggtg | cccatcctgg | tcgagctgga | cggcgacgta | 120 |
| aacggccaca | agttcagcgt | gtccggcgag | ggcgagggcg | atgccaccta | cggcaagctg | 180 |
| accctgaagt | tcatctgcac | caccggcaag | ctgcccgtgc | cctggcccac | cctcgtgacc | 240 |
| accttcggct | acggcctgat | gtgcttcgcc | cgctacccg | accacatgaa | gcagcacgac | 300 |
| ttcttcaagt | ccgccatgcc | cgaaggctac | gtccaggagc | gcaccatctt | cttcaaggac | 360 |
| gacggcaact | acaagacccg | cgccgagtg | aagttcgagg | gcgacaccct | ggtgaaccgc | 420 |
| atcgagctga | agggcatcga | cttcaaggag | gacggcaaca | tcctggggca | aagctggag | 480 |
| tacaactaca | acagccacaa | cgtctatatc | atggccgaca | agcagaagaa | cggcatcaag | 540 |
| gtgaacttca | agatccgcca | caacatcgag | gacggcagcg | tgcagctcgc | cgaccactac | 600 |
| cagcagaaca | cccccatcgg | cgacggcccc | gtgctgctgc | ccgacaacca | ctacctgagc | 660 |
| taccagtccg | ccctgagcaa | agaccccaac | gagaagcgcg | atcacatggt | cctgctggag | 720 |
| ttcgtgaccg | ccgccgggat | cactctcggc | atggacgagc | tgtacaagga | tcctgctggt | 780 |

```
gctgctgcgg ccgctggggc ccacccaact tttctataca aagttgtcat gcatcgtcag    840
ccatctcctc acgccttcag gtagtaaaag tatactaagc cgcagggcac cacaacgcaa    900
cacgtggtgc ctgcctgcct ccttccttgt tcgctttgcg gcgcgagcgt tttgtctgtt    960
gttgtctccc ttgggaccgg cgcgtccggc tggctcacta ccactaacgt gttgttgcct   1020
gccttgtgcg gcgcccgtgg ttcgcattgc gtttgcagca gcagcggcag ctgggcggag   1080
cagggcgcgg gcgggtaccg ccacggcagg gacggcgcca ccttcctcct ccccgagctc   1140
ctccagcgca gtaataacgc cgccctgccc cttgtttatc cgcctgcctg cgtattttgt   1200
ttcctttctt tttcttcttg ttggatttct catggctgtt ggttcacgc gcgcgcatcg   1260 cgggggctaa tgtgaaggcc ccaaccccag ctccaagtcc tccagcgccg ccaccttcgt   1320
gccgccgctc gccgccgcgg tgagttcact gactgagaat gagatacggt tcgttctccg   1380
ccgcggcttc ttcactttga gcgtgaatga catggaggct ctctctggcg tcttttttgtc   1440 tgcagcatgg aggaggagta gcggccccgt ttggcatggc gccgctggga gtggcggcgg   1500
cggacgaagc ccggttctgc atgacgccgt ggtcagcggc ggcgcacttc gagaactggg   1560
gcgactccgg catcgtcgtc accagcccgc tcgccgagac ggcctccacc gacgtcgaca   1620
tggtctgctc ctcaatactc agcttccatc catcttcatc cgcatgcaca gtatatatgc   1680
ctgccatgaa ctccgcctgg agtatatgta tatgccgtga cgtgtgactc caccgccgtc   1740
gtcgtagggt ggaggtggag ccatggcgca gagcgtcgac ggacatgaca actcattgcc   1800
ggcgtgcaag gtggagccca gggatcacaa ggtgcgctat gccatgtcac gtgaacacgt   1860
cgtcgtggtc ccaaaaagga actagaagag cagcagatgt gattgtggtt tttgtgctgt   1920
gtcatggcag gcgcagagga ggcttgcgca aaaccgcgag gcggcccgga aaagccggat   1980
gaggaagaag gtgatccccc ttcccctcac gggaagcttc tgtacattat gctatgcttg   2040
caagttgcat tccatcctgt cttcttcttg ctcagtaccc ccctgtttat ttaccctgac   2100
gggaggctta ctgagttttg tctacagttt tactgtacca tgctgtcact gtttccactt   2160
gcaagatcgc tgaagcactg tgcaaattcg ctctgtaggc gtacattgtg gagctggaaa   2220
acagccggtc caagctgtcc catcttgagc aggagcttca aagggcaagg cagcaggtga   2280
actcctgatc tgttttcctc tgaagaacga aacgatccat actacttcga cgctgattgt   2340
ctatgggctg taaatacagg ggatgttcat tgcaagtgga cgctccggag atcatggatg   2400
ctccactgga ggcagatgat cttttttttct tctcttttac attgctcagc tcttgttctc   2460
tgaattctga tcctgtgcaa tgtaaagcct aacctgtgtc cttgcaggtg cgttggcgtt   2520
cgacctggag tacgcgcggt ggctggacga gcaccagcac cacatgaacg acctccgggt   2580
ggccctgagc gcgcagatcg gcgacgacga cctgggcgtg ctggtggacg cgcgatgct   2640 gcactacgac cagatgttcc ggctcaaggg cgtggccacg aggacggacg tgttccacgt   2700
gctgtcgggc atgtgatga gccccgcgga gcggttcttc atgtggctgg gcgggttccg   2760
gtcgtcggag ctgctcaagg tgctggcgcg gcacgtggag ccgctgacgg agcagcagct   2820
ggtgggcatc tgcggcctgc agcagtcgct gcagcaggcc gaggacgcgc tgtcgcaggg   2880
gatggaggcc ctgcagcagg ccctcgggga cacgctcgcc gccgccgcca cgccgtgcgc   2940
cgccgacagc gtcaccaact acatgggcca gatggccgtc gccatgagca agctcgccac   3000
cgtggagaac ttcctccgcc aggcggacct gctgcggcag cagacgctga agcaggtgcg   3060
ccggatcctg accacgcgcc aagcgcgcgc gcgctgctc gtcatcagtg actacttctc   3120
gcggctccgt gcgctcagct ccctgtggct gacgcggccg acggattga                3169
```

<210> SEQ ID NO 19
<211> LENGTH: 3187
<212> TYPE: DNA
<213> ORGANISM: Artificial Sequence
<220> FEATURE:
<223> OTHER INFORMATION: RFP-FEA4 fusion protein-coding sequence

<400> SEQUENCE: 19

```
atgacaactt tgtatacaaa agttgcaggc cggcctggag gtggaggtgg agctggccgg      60
cctggaggtg gaggtggagc tgcctcctcc gaggacgtca tcaaggagtt catgcgcttc     120
aaggtgcgca tggagggctc cgtgaacggc acgagttcg agatcgaggg cgagggcgag     180
ggccgcccct acgagggcac ccagaccgcc aagctgaagg tgaccaaggg cggccccctg     240
cccttcgcct gggacatcct gtcccctcag ttccagtacg gctccaaggc ctacgtgaag     300
caccccgccg acatccccga ctacttgaag ctgtccttcc ccgagggctt caagtgggag     360
cgcgtgatga cttcgagga cggcggcgtg gtgaccgtga cccaggactc ctccctgcag     420
gacggcgagt tcatctacaa ggtgaagctg cgcggcacca cttcccctc cgacggcccc     480
gtaatgcaga agaagaccat gggctgggag gcctccaccg agcggatgta ccccgaggac     540
ggcgccctga agggcgagat caagatgagg ctgaagctga aggacggcgg ccactacgac     600
gccgaggtca agaccaccta catggccaag aagcccgtgc agctgcccgg cgcctacaag     660
accgacatca gctggacat cacctcccac aacgaggact acaccatcgt ggaacagtac     720
gagcgcgccg agggccgcca ctccaccggc gccgatcctg ctggtgctgc tgcggccgct     780
ggggccgatc ctgctggtgc tgctgcggcc gctgggccc acccaacttt tctatacaaa     840
gttgtcatgc atcgtcagcc atctcctcac gccttcaggt agtaaaagta tactaagccg     900
cagggcacca caacgcaaca cgtggtgcct gcctgcctcc ttccttgttc gctttgcggc     960
gcgagcgttt tgtctgttgt tgtctcccctt gggaccggcg cgtccggctg gctcactacc    1020
actaacgtgt tgttgcctgc cttgtgcggc gcccgtggtt cgcattgcgt ttgcagcagc    1080
agcggcagct gggcggagca gggcgcgggc gggtaccgcc acggcaggga cggcgccacc    1140
ttcctcctcc ccgagctcct ccagcgcagt aataacgccg ccctgcccct tgtttatccg    1200
cctgcctgcg tattttgttt cctttctttt tcttcttgtt ggatttctca tggctgttgg    1260
ttgcacgcgc gcgcatcgcg ggggctaatg tgaaggcccc aaccccagct ccaagtcctc    1320
cagcgccgcc accttcgtgc cgccgctcgc cgccgcggtg agttcactga ctgagaatga    1380
gatacggttc gttctccgcc gcggcttctt cactttgagc gtgaatgaca tggaggctct    1440
ctctggcgtc tttttgtctg cagcatggag gaggagtagc ggccccgttt ggcatggcgc    1500
cgctgggagt ggcggcggcg gacgaagccc ggttctgcat gacgccgtgg tcagcggcgg    1560
cgcacttcga gaactggggc gactccggca tcgtcgtcac cagcccgctc gccgagacgg    1620
cctccaccga cgtcgacatg gtctgctcct caatactcag cttccatcca tcttcatccg    1680
catgcacagt atatatgcct gccatgaact ccgcctggag tatatgtata tgccgtgacg    1740
tgtgactcca ccgccgtcgt cgtagggtgg aggtggagcc atggcgcaga gcgtcgacgg    1800
acatgacaac tcattgccgg cgtgcaaggt ggagcccagg gatcacaagg tgcgctatgc    1860
catgtcacgt gaacacgtcg tcgtggtccc aaaaaggaac tagaagagca gcagatgtga    1920
ttgtggtttt tgtgctgtgt catggcaggc gcagaggagg cttgcgcaaa accgcgaggc    1980
ggcccggaaa agccggatga ggaagaaggt gatcccccctt cccctcacgg gaagcttctg    2040
```

| | |
|---|---|
| tacattatgc tatgcttgca agttgcattc catcctgtct tcttcttgct cagtaccccc | 2100 |
| ctgtttatttt accctgacgg gaggcttact gagttttgtc tacagttta ctgtaccatg | 2160 |
| ctgtcactgt ttccacttgc aagatcgctg aagcactgtg caaattcgct ctgtaggcgt | 2220 |
| acattgtgga gctggaaaac agccggtcca agctgtccca tcttgagcag agcttcaaa | 2280 |
| gggcaaggca gcaggtgaac tcctgatctg ttttcctctg aagaacgaaa cgatccatac | 2340 |
| tacttcgacg ctgattgtct atgggctgta aatacagggg atgttcattg caagtggacg | 2400 |
| ctccggagat catggatgct ccactggagg cagatgatct tttttcttc tcttttacat | 2460 |
| tgctcagctc ttgttctctg aattctgatc ctgtgcaatg taaagcctaa cctgtgtcct | 2520 |
| tgcaggtgcg ttggcgttcg acctggagta cgcgcggtgg ctggacgagc accagcacca | 2580 |
| catgaacgac ctccgggtgg ccctgagcgc gcagatcggc gacgacgacc tgggcgtgct | 2640 |
| ggtggacggc gcgatgctgc actacgacca gatgttccgg ctcaagggcg tggccacgag | 2700 |
| gacggacgtg ttccacgtgc tgtcgggcat gtggatgagc cccgcggagc ggttcttcat | 2760 |
| gtggctgggc gggttccggt cgtcggagct gctcaaggtg ctggcgcggc acgtggagcc | 2820 |
| gctgacggag cagcagctgg tgggcatctg cggcctgcag cagtcgctgc agcaggccga | 2880 |
| ggacgcgctg tcgcagggga tggaggccct gcagcaggcc ctcggggaca cgctcgccgc | 2940 |
| cgccgccacg ccgtgcgccg ccgacagcgt caccaactac atgggccaga tggccgtcgc | 3000 |
| catgagcaag ctcgccaccg tggagaactt cctccgccag gcggacctgc tgcggcagca | 3060 |
| gacgctgaag caggtgcgcc ggatcctgac cacgcgccaa gccgcgcgcg cgctgctcgt | 3120 |
| catcagtgac tacttctcgc ggctccgtgc gctcagctcc ctgtggctga cgcggccgac | 3180 |
| ggattga | 3187 |

<210> SEQ ID NO 20
<211> LENGTH: 1591
<212> TYPE: DNA
<213> ORGANISM: Zea mays

<400> SEQUENCE: 20

| | |
|---|---|
| ttcggcgtac gcacacggac gggagctgtc gttggttggt tgcgctgaga ctgtaatctg | 60 |
| tatccgttgt gagatggggt gaccatgcgg attcatcagg cagaaacggc gaatgtgtct | 120 |
| agctttagtt ttggctacca ttcagcttca tcagtgaggc tagagtagag cgatttcggt | 180 |
| gcgcatgtcc aggcttttgc tccgcgttca ttgtctcggc tgcaattgcc tgcggtctgc | 240 |
| agattccctc gtcatgggct catgcccagc tgcgcgccgg ccgcgtgccg tggaatgacg | 300 |
| gaatgaggaa gctgggtccg cggcaatcat gcgccttgcc cgcctagcgt gtcgactgca | 360 |
| tgcagtcctg cggggacctg atcgcgtggc taccgatcac tactgcactg acactggata | 420 |
| ccgtgggtgc atagatgtgc aaaaggactc ggtactggct aacaaggggg tgtttggtta | 480 |
| cccctgctaa agtttagctc gggtcacatt aagtgtttga cttttaaata agagtataaa | 540 |
| atatagaccc aactaactga actaaatttg tctcgtcttt taatcttcgg ctgacaaatt | 600 |
| agttttataa tccgactaca tttaatacc gaatcggagg ttcaaacatt cgatgagaca | 660 |
| ggggctaaat tttagcggtt tgtaaccaaa caccccctaa ggctgtgtcc aacaactaac | 720 |
| gctataacga actatacgtt aaatatagcg ttgttgtgtc caacgagtaa cgctataacg | 780 |
| tcatatagcg ttctccgctc gctcgcccac acgcgtccag caatgtgaat caatacgaca | 840 |
| taaagtagat taaacacaga agacatattt agcatgaaaa accctccaa agcgaaggag | 900 |
| aaaaaaccac ggacaccgac ctacaacaat atcactattt ttcggggttgt tacagatcac | 960 |

-continued

```
aagagattta caatgaggtg acgatctctt gcggattata agtgtattta tagagacgaa    1020
accctaaggt gagtagagaa cactccggcc caagcctccc gacgacgggc ctccgcttcg    1080
ctcgccaact tggccgcatt cttcagaatt ttgatcacaa actcaacaaa cgatacttta    1140
aaatttagag gacgtcaaga cttccgagcg tgcgctatcc gggtgagggc ttgggctccc    1200
gtcacgatga aatgtccgcg cgcgcagttc ccagaaggag gcgtcgcggt gtgggtcaaa    1260
atgcataata aatatagtca gtccggacct ttaaaattta tttacaatat ttattttcgg    1320
tacacaaacg tgtgtaacat aatattcatt tcatattaat tttttgtaat tatattatgt    1380
attctgacta gattttatcg tgacgggagc tacaccgacg tcttttaaag tgtgttgtaa    1440
aggacaagaa tattttttta gggatagaat ttaggagacg ttgctagagg taggccaagc    1500
atggtctggt agcatcgagt tacatatgat aaggtacggt gagcatgctc acttgtttca    1560
agaattgtat gatttaatgt ttgctttcgc t                                   1591
```

NUCLEOTIDE SEQUENCES ENCODING FASCIATED EAR4 (FEA4) AND METHODS OF USE THEREOF

CROSS REFERENCE TO RELATED APPLICATIONS

This application claims the benefit of U.S. Provisional Application No. 61/610,730, filed Mar. 14, 2012, and U.S. Provisional Application No. 61/759,342, filed Jan. 31, 2013, the entire content of each is herein incorporated by reference.

GOVERNMENT SUPPORT

The invention described herein was made in whole or in part with government support under United States Grant No. 0604923 awarded by the National Science Foundation under the Plant Genome Research Project Grants Program. The United States Government has certain rights in the invention.

FIELD OF THE INVENTION

The invention relates to the field of the genetic manipulation of plants, particularly the modulation of gene activity and development in plants.

BACKGROUND OF THE INVENTION

Leaves and the axillary meristems that generate branches and flowers are initiated in regular patterns from the shoot apical meristem (SAM). The cells of the shoot apical meristem summit serve as stem cells that divide to continuously displace daughter cells to the surrounding regions, where they are incorporated into differentiated leaf or flower primordia. The meristems are thus capable of regulating their size during development by balancing cell proliferation with the incorporation of cells into new primordia. The SAM provides all aerial parts of plant body. The central concept of stem cells regulation is known by the signal pathway of CLAVATA/WUSCHEL (CLV/WUS) genes. Loss of CLV1, CLV2, or CLV3 activity in *Arabidopsis* causes accumulation of undifferentiated cells in the shoot apex, indicating that CLV genes together promote the timely transition of stem cells into differentiation pathways, or repress stem cell division, or both (Fletcher et al. (1999) *Science* 283:1911-1914; Taguchi-Shiobare et al. (2001) *Genes and Development* 15:2755-5766; and, Trotochaud et al. (1999) *Plant Cell* 11:393-405; Merton et al. (1954) *Am. J. Bot.* 41:726-32 and Szymkowiak et al. (1992) *Plant Cell* 4:1089-100; Yamamoto et al. (2000) *Biochim. Biophys. Acta.* 1491:333-40). The maize orthologues of CLV1/2 are TD1 and FEA2, that have been reported (Taguchi-Shiobare et al. (2001) *Genes Dev.* 65 15:2755-66). It is desirable to be able to control the size and appearance of shoot and floral meristems, to give increased yields of leaves, flowers, and fruit. Accordingly, it is an object of the invention to provide novel methods and compositions for the modulation of meristem development.

SUMMARY OF THE INVENTION

In one embodiment, the current invention provides a method of producing a transgenic plant with decreased expression of endogenous Fea4, the method comprising the steps of (a) introducing into a regenerable plant cell a recombinant construct comprising a polynucleotide sequence operably linked to a promoter, wherein the expression of the polynucleotide sequence reduces endogenous Fea4 expression; (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and exhibits a decrease in expression of Fea4, when compared to a control plant not comprising the recombinant DNA construct.

In another embodiment, the current invention provides a method of producing a transgenic plant with decreased expression of endogenous Fea4, the method comprising the steps of (a) introducing into a regenerable plant cell a recombinant DNA construct comprising an isolated polynucleotide operably linked, in sense or antisense orientation, to a promoter functional in a plant, wherein the polynucleotide comprises: (i) the nucleotide sequence of SEQ ID NO:1 or 2; (ii) a nucleotide sequence with at least 90% sequence identity, based on the Clustal W method of alignment, when compared to SEQ ID NO:1 or 2; (iii) a nucleotide sequence of at least 100 contiguous nucleotides of SEQ ID NO:1 or 2; (iv) a nucleotide sequence that can hybridize under stringent conditions with the nucleotide sequence of (i); or (v) a modified plant miRNA precursor, wherein the precursor has been modified to replace the miRNA encoding region with a sequence designed to produce a miRNA directed to SEQ ID NO:1 or 2; (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and exhibits a decrease in expression of Fea4, when compared to a control plant not comprising the recombinant DNA construct.

One embodiment of the invention is a method of producing a transgenic plant with alteration of an agronomic characteristic, the method comprising the steps of (a) introducing into a regenerable plant cell a recombinant DNA construct comprising an isolated polynucleotide operably linked to at least one regulatory sequence, wherein the polynucleotide encodes a fragment or a variant of a polypeptide having an amino acid sequence of at least 80% sequence identity, based on the Clustal W method of alignment, when compared to SEQ ID NO:3, wherein the fragment or the variant confers a dominant-negative phenotype in the regenerable plant cell; (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and exhibits an alteration of at least one agronomic characteristic selected from the group consisting of: ear meristem size, kernel row number, leaf number, inflorescence number, branching within the inflorescence, flower number, fruit number, seed number, plant height, biomass and yield, when compared to a control plant not comprising the recombinant DNA construct.

Another embodiment of the current invention is the above method wherein expression of the polypeptide of part (a) in a plant line having the fea4 mutant genotype is capable of partially or fully restoring the wild-type phenotype.

One embodiment of the current invention is a method of identifying a weaker allele of fea4, the method comprising the steps of (a) performing a genetic screen on a population of mutant maize plants (b) identifying one or more mutant maize plants that exhibit weak fea4 phenotype than a fea4 null plant; and (c) identifying the weak fea4 allele from the mutant maize plant with weaker fea4 phenotype.

One embodiment of the current invention is a method of identifying a weaker allele of fea4, the method comprising the steps of: (a) gene shuffling using SEQ ID NO:1 or 2; (b) transforming the shuffled sequences from step (a) into a population of regenerable plant cells; (c) regenerating a population of transformed plants from the population of transformed regenerable plant cells of step (b); (d) screening the population of transformed plants from step (c) for weak fea4 phenotype; and (e) identifying the weak fea4 allele from the transformed plant exhibiting weak fea4 phenotype.

One embodiment of the invention is a plant in which expression of the endogenous Fea4 gene is inhibited relative to a control plant. Another embodiment of the current invention is a method of making said plant, the method comprising the steps of (a) introducing a mutation into the endogenous Fea4 gene; and (b) detecting the mutation, wherein the mutation is effective in inhibiting the expression of the endogenous Fea4 gene. In one embodiment, the steps (a) and (b) are done using Targeting Induced Local Lesions IN Genomics (TILLING) method. In another embodiment, the mutation is a site-specific mutation.

One embodiment of the invention is a plant that exhibits weaker fea4 phenotype relative to a wild-type plant. Another embodiment is a method of making said plant wherein the method comprises the steps of: (a) introducing a transposon into a germplasm containing an endogenous Fea4 gene; (b) obtaining progeny of the germplasm of step (a); (c) and identifying a plant of the progeny of step (b) in which the transposon has inserted into the endogenous Fea4 gene and a reduction of expression of Fea4 is observed. Step (a) may further comprise introduction of the transposon into a regenerable plant cell of the germplasm by transformation and regeneration of a transgenic plant from the regenerable plant cell, wherein the transgenic plant comprises in its genome the transposon.

In one embodiment, the methods described above wherein the method further comprises the steps of (a) introducing into a regenerable plant cell a recombinant construct comprising the weak fea4 allele identified by the methods described above; (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and exhibits a weak fea4 phenotype, when compared to a control plant not comprising the recombinant DNA construct.

Another embodiment is a method of producing a transgenic plant with an alteration in agronomic characteristic, the method comprising (a) introducing into a regenerable plant cell a recombinant DNA construct comprising an isolated polynucleotide operably linked, in sense or antisense orientation, to a promoter functional in a plant, wherein the polynucleotide comprises: (i) the nucleotide sequence of SEQ ID NO:1 or 2; (ii) a nucleotide sequence with at least 90% sequence identity, based on the Clustal W method of alignment, when compared to SEQ ID NO:1 or 2; (iii) a nucleotide sequence of at least 100 contiguous nucleotides of SEQ ID NO:1 or 2; (iv) a nucleotide sequence that can hybridize under stringent conditions with the nucleotide sequence of (i); or (v) a modified plant miRNA precursor, wherein the precursor has been modified to replace the miRNA encoding region with a sequence designed to produce a miRNA directed to SEQ ID NO:1 or 2; (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and exhibits an alteration in at least one agronomic characteristic selected from the group consisting of: enlarged ear meristem, kernel row number, seed number, plant height, biomass and yield, when compared to a control plant not comprising the recombinant DNA construct. Another embodiment is the plant produced by this method.

One embodiment is a method of expressing a heterologous polynucleotide in a plant, the method comprising (a) transforming a regenerable plant cell with a recombinant DNA construct comprising a heterologous polynucleotide operably linked to a second polynucleotide, wherein the second polynucleotide is a Fea4 promoter (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and further wherein the heterologous polynucleotide is expressed in the transgenic plant. Another embodiment is the plant comprising in its genome a recombinant DNA construct comprising a heterologous polynucleotide operably linked to a second polynucleotide, wherein the second polynucleotide is a Fea4 promoter and wherein the heterologous polynucleotide is expressed in the plant.

Another embodiment is a method of identifying a first maize plant or a first maize germplasm that has an alteration of at least one agronomic characteristic, the method comprising detecting in the first maize plant or the first maize germplasm at least one polymorphism of a marker locus that is associated with said phenotype, wherein the marker locus encodes a polypeptide comprising an amino acid sequence selected from the group consisting of: a) an amino acid sequence having at least 90% and less than 100% sequence identity to SEQ ID NO:3, wherein expression of said polypeptide in a plant or plant part thereof results in an alteration of at least one agronomic characteristic selected from the group consisting of: ear meristem size, kernel row number, inflorescence number, branching within the inflorescence, flower number, fruit number, and seed number, when compared to a control plant, wherein the control plant comprises SEQ ID NO:3.

The invention includes a recombinant DNA construct comprising an isolated polynucleotide of the current invention operably linked, in sense or antisense orientation, to a promoter that is shoot apical meristem specific or shoot apical meristem preferred.

This invention includes a vector, cell, plant, or seed comprising any of the recombinant DNA constructs described in the present invention.

The invention encompasses plants produced by the methods described herein.

The invention also encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant is selected from the group consisting of: *Arabidopsis*, tomato, maize, soybean, sunflower, sorghum, canola, wheat, alfalfa, cotton, rice, barley, millet, sugar cane and switchgrass.

In one embodiment, the plant comprising the recombinant constructs described in the present invention is a monocotyledonous plant. In another embodiment, the plant comprising the recombinant constructs described in the present invention is a maize plant.

BRIEF DESCRIPTION OF THE DRAWINGS AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIG. 1A shows the position of fea4 on chromosome 6. FIG. 1B shows the position of site-specific mutations and Mu transposon insertions in fea4. FIG. 1C shows the domains within the FEA4 protein.

FIG. 2A shows the vegetative phenotype of the fea4 mutation. FIG. 2B compares the tassels of wild-type (left) to fea4 mutant (right). FIG. 2C compares ears of wild-type (left) to fea4 mutant (right). FIG. 2D and FIG. 2E show SEM pictures of immature ears for fea4 and wild-type, respectively.

FIG. 3A shows the ear and tassel phenotypes of fea4, ramosa2 and the fea4/ramosa2 double mutant. FIG. 3B shows the ear and tassel phenotypes of fea4, ramosa1 and the fea4/ramosa1 double mutant. FIG. 3C shows the ear and tassel phenotypes of fea4, ramosa3 and the fea4/ramosa3 double mutant.

FIG. 4A shows the ear phenotype of a double mutant between fea4 and the CLAVATA2 ortholog, fea2. FIG. 4B shows the vegetative phenotype of the fea4/fea2 double mutant.

Figure 6A:
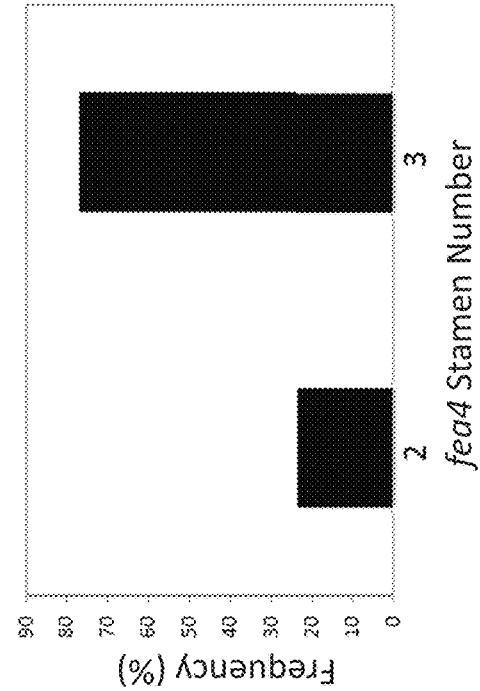
Figure 6B:
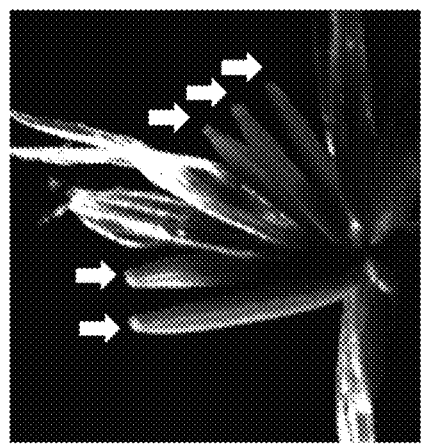
Figure 6C:
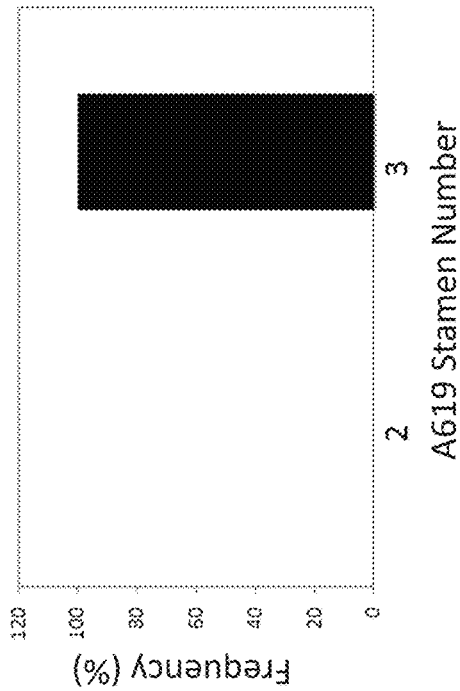
Figure 6D:
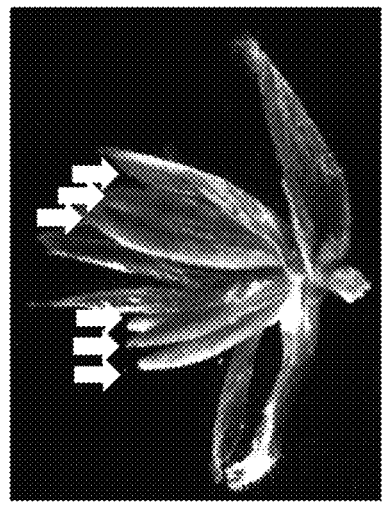

FIG. 6A shows stamens of a fea4 mutant in an A619 background. FIG. 6B gives the frequency of stamen number in the fea4 mutant line. FIG. 6C shows stamens of wild-type (WT) A619. FIG. 6D gives the frequency of stamen number in the WT line.

Figure 7:
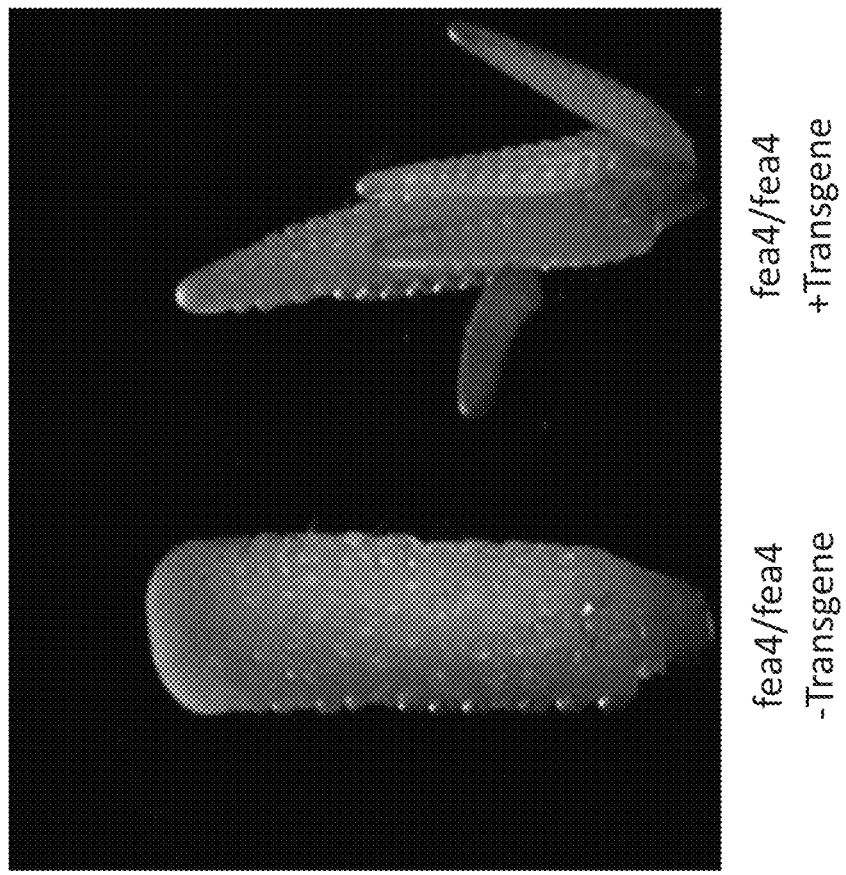

FIG. 7 compares a fea4/fea4 homozygous line without a FEA4 transgene (left) to a fea4/fea4 homozygous line that has been transformed with a translational fusion of the FEA4 coding sequence to yellow fluorescent protein (YFP), under control of the native promoter.

FIG. 8A-8D show meristems from F2 plants of wild-type, fea2, fea4 and fea4/fea2 mutant lines, respectively. FIG. 8E shows the meristem size in millimeters for each line.

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

SEQ ID NO:1 is the nucleotide sequence of the genomic wild-type Fea4 gene.

SEQ ID NO:2 is the nucleotide sequence of the coding region of the wild-type Fea4.

SEQ ID NO:3 is the amino acid sequence of wild-type FEA4 protein.

SEQ ID NO:4 is the nucleotide sequence of the genomic mutant fea4-O allele.

SEQ ID NO:5 is the nucleotide sequence of the coding region of the mutant fea4-0 allele.

SEQ ID NO:6 is the amino acid sequence encoded by the mutant fea4-O allele.

SEQ ID NO:7 is the nucleotide sequence of the genomic mutant fea4-rel*09-5171 allele.

SEQ ID NO:8 is the nucleotide sequence of the coding region of the mutant fea4-rel*09-5171 allele.

SEQ ID NO:9 is the amino acid sequence encoded by the mutant fea4-rel*09-5171 allele.

SEQ ID NO:10 is the nucleotide sequence of the genomic AT1G68640 locus, for the *Arabidopsis* PERIANTHIA (PAN) gene.

SEQ ID NO:11 is the nucleotide sequence of a cDNA for the AT1G68640 locus.

SEQ ID NO:12 is the amino acid sequence of protein encoded by the AT1G68640 locus.

SEQ ID NO:13 is the nucleotide sequence encoding Sb10g009592.1, a FEA4 homolog from sorghum.

SEQ ID NO:14 is the amino acid sequence of Sb10g009592.1, a FEA4 homolog from sorghum.

SEQ ID NO:15 is the nucleotide sequence encoding LOC_Os06g15480.1, a FEA4 homolog from rice.

SEQ ID NO:16 is the amino acid sequence of LOC_Os06g15480.1, a FEA4 homolog from rice.

SEQ ID NO:17 is the nucleotide sequence of the FEA4 promoter.

SEQ ID NO:18 is the nucleotide sequence encoding a YFP-FEA4 fusion protein.

SEQ ID NO:19 is the nucleotide sequence encoding a RFP-FEA4 fusion protein.

SEQ ID NO:20 is the nucleotide sequence of the FEA4 3'-UTR.

The sequence descriptions and Sequence Listing attached hereto comply with the rules governing nucleotide and/or amino acid sequence disclosures in patent applications as set forth in 37 C.F.R. §1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, or by agricultural observations such as osmotic stress tolerance or yield.

"Agronomic characteristic" is a measurable parameter including but not limited to, ear meristem size, tassel size, greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to a polynucleotide sequence that when transcribed, processed, and/or translated results in the production of a polypeptide sequence.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches. Silencing may be targeted to coding regions or non-coding regions, e.g., introns, 5'-UTRs and 3'-UTRs, or both.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., Plant J. 16:651-659 (1998); and Gura, Nature 404:804-808 (2000)). Cosuppression constructs may contain sequences from coding regions or non-coding regions, e.g., introns, 5'-UTRs and 3'-UTRs, or both.

Another variation describes the use of plant viral sequences to direct the suppression of proximal mRNA encoding sequences (PCT Publication No. WO 98/36083 published on Aug. 20, 1998).

RNA interference refers to the process of sequence-specific post-transcriptional gene silencing in animals mediated by short interfering RNAs (siRNAs) (Fire et al., Nature 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., Trends Genet. 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., Science 294:853-858 (2001), Lagos-Quintana et al., Curr. Biol. 12:735-739 (2002); Lau et al., Science 294:858-862 (2001); Lee and Ambros, Science 294:862-864 (2001); Llave et al., Plant Cell 14:1605-1619 (2002); Mourelatos et al., Genes. Dev. 16:720-728 (2002); Park et al., Curr. Biol. 12:1484-1495 (2002); Reinhart et al., Genes. Dev. 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition; and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

The term "locus" generally refers to a genetically defined region of a chromosome carrying a gene or, possibly, two or more genes so closely linked that genetically they behave as a single locus responsible for a phenotype. When used herein with respect to Fea4, the "Fea4 locus" shall refer to the defined region of the chromosome carrying the Fea4 gene including its associated regulatory sequences.

A "gene" shall refer to a specific genetic coding region within a locus, including its associated regulatory sequences. One of ordinary skill in the art would understand that the associated regulatory sequences will be within a distance of about 4 kb from the Fea4 coding sequence, with the promoter located upstream.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells, that can be cultured into a whole plant.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal W method of alignment.

The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB.

After alignment of the sequences, using the Clustal W program, it is possible to obtain "percent identity" and "divergence" values by viewing the "sequence distances" table on the same program; unless stated otherwise, percent identities and divergences provided and claimed herein were calculated in this manner.

The present invention includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:3, 6, 9, 12, 14 or 16; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. The polypeptide is preferably a FEA4 polypeptide. The polypeptide preferably has FEA4 activity.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:3, 6, 9, 12, 14 or 16. The polypeptide is preferably a FEA4 polypeptide. The polypeptide preferably has FEA4 activity.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:1, 2, 4, 5, 7, 8, 10, 11, 13 or 15; or (ii) a full complement of the nucleic acid sequence of (i). Any of the foregoing isolated polynucleotides may be utilized in any recombinant DNA constructs (including suppression DNA constructs) of the present invention. The polypeptide is preferably a FEA4 polypeptide. The polypeptide preferably has FEA4 activity.

An isolated polynucleotide comprising a nucleotide sequence, wherein the nucleotide sequence is hybridizable under stringent conditions with a DNA molecule comprising the full complement of SEQ ID NO:1, 2, 4, 5, 7, 8, 10, 11, 13 or 15. The polypeptide is preferably a FEA4 polypeptide. The polypeptide preferably has FEA4 activity.

An isolated polynucleotide comprising a nucleotide sequence, wherein the nucleotide sequence is derived from SEQ ID NO:1, 2, 4, 5, 7, 8, 10, 11, 13 or 15 by alteration of one or more nucleotides by at least one method selected from the group consisting of: deletion, substitution, addition and insertion. The polypeptide is preferably a FEA4 polypeptide. The polypeptide preferably has FEA4 activity.

An isolated polynucleotide comprising a nucleotide sequence, wherein the nucleotide sequence corresponds to an allele of SEQ ID NO:1, 2, 4, 5, 7, 8, 10, 11, 13 or 15.

In one embodiment, the present invention includes recombinant DNA constructs (including suppression DNA constructs). The recombinant DNA construct (including suppression DNA constructs) may comprise a polynucleotide of the present invention operably linked, in sense or antisense orientation, to at least one regulatory sequence (e.g., a promoter functional in a plant). The polynucleotide may comprise 100, 200, 300, 400, 500, 600, 700, 800, 900 or 1000 contiguous nucleotides of SEQ ID NO:1, 2, 4, 5, 7, 8, 10, 11, 13 or 15. The polynucleotide may encode a polypeptide of the present invention.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

It is well understood by those skilled in the art that different promoters may direct the expression of a gene in different tissues or cell types, or at different stages of development, or in response to different environmental conditions.

Promoters that can be used for this invention include, but are not limited to, shoot apical meristem specific promoters and shoot apical meristem preferred promoters. Maize knotted 1 promoter, and promoters from genes that are known to be expressed in maize SAM can be used for expressing the polynucleotides disclosed in the current invention. Examples of such genes include, but are not limited to Zm phabulosa, terminal ear1, rough sheath2, rolled leaf1, zyb14, narrow sheath (Ohtsu, K. et al (2007) *Plant Journal* 52, 391-404). Promoters from orthologs of these genes from other species can be also be used for the current invention.

Examples of *Arabidopsis* promoters from genes with SAM-preferred expression include, but are not limited to, clv3, aintegumenta-like (ail5, ail6, and ail7) and terminal ear like1, clavata1, wus, shootmeristemless, terminal flower1 (Yadav et al (2009) *Proc Natl Acad Sci USA*. March 24).

PCT Publication Nos. WO 2004/071467 and U.S. Pat. No. 7,129,089 describe the synthesis of multiple promoter/gene/terminator cassette combinations by ligating individual promoters, genes, and transcription terminators together in unique combinations. Generally, a NotI site flanked by the suitable promoter is used to clone the desired gene. NotI sites can be added to a gene of interest using PCR amplification with oligonucleotides designed to introduce NotI sites at the 5' and 3' ends of the gene. The resulting PCR product is then digested with NotI and cloned into a suitable promoter/NotI/terminator cassette. Although gene cloning into expression cassettes is often done using the NotI restriction enzyme, one skilled in the art can appreciate that a number of restriction enzymes can be utilized to achieve the desired cassette. Further, one skilled in the art will appreciate that other cloning techniques including, but not limited to, PCR-based or recombination-based techniques can be used to generate suitable expression cassettes.

In addition, WO 2004/071467 and U.S. Pat. No. 7,129,089 describe the further linking together of individual promoter/gene/transcription terminator cassettes in unique combinations and orientations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination or orientations. In so doing, any combination and orientation of shoot apical meristem-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

fasciated ear4 (fea4), previously called fea1905 (Pautler et al. Abstract from the 52$^{nd}$ Annual Maize Genetics Conference; Mar. 18-21, 2010, Trento, Italy), is a novel fasciated ear mutant of maize. The primary defects in this mutant are fasciated ears and thickened tassel due to an enlarged inflorescence meristem. Additional reproductive phenotypes include a reduction in the number of long tassel branches. Vegetative phenotypes such as semi-dwarfism and shorter, wider leaves may be present in certain environmental conditions, such as short days.

The term "fasciation", from the Latin fascis, meaning bundle, describes variations in plant form resulting from proliferative growth.

The terms "wild-type fea4 gene", "fea4 wt gene", "Fea4 gene" and "FEA4 gene" are used interchangeably herein.

fea4 was discovered by screening an EMS mutagenized inbred maize population for mutants with fasciated ears. The genetic background of the mutation is the A619 inbred line, but the phenotype is manifest upon introgression to many other inbred lines as well.

fea4 was mapped to the long arm of chromosome 6 by genotyping approximately 500 mutants from an F2 mapping population. Sequencing of one candidate gene, which encoded a bZIP class transcription factor of 432 amino acids, revealed a C-to-T base transition, resulting in an early stop codon. C-to-T (G-to-A) mutations are a consequence of chemical mutagenesis with EMS. A second allele, fea4-rel*09-5171, with a stop codon was identified, confirming that the correct gene had been isolated.

FEA4 is orthologous to the *Arabidopsis* gene PERIANTHIA (PAN), which has a defect in the number of floral organs. pan mutants have five petals and five sepals in the outer whorls, instead of four (Running, M P, Meyerowitz, E M. 1996 Development 122:1261-9; Chuang, C., et al. 1999 Genes and Development 13:333-344). When grown in short day conditions (approximately 8 hours of light, and 16 hours of darkness) pan mutants display indeterminate floral meristems, resulting in the production of many aberrant floral organs (Maier, A., et al. 2009 Development 136:1613-1620).

FEA4 is expressed in immature ear and tassel primordia according to RNA-seq transcriptome profiling. The expression is highest at the tip of the ear (inflorescence meristem) and decreases in the middle and basal portion of the ear. In addition, expression decreases as the tassel primordia increase in size from 2-7 mm.

Our analysis of fea2/fea4 double mutants indicate that fea4 may act in parallel to the CLAVATA2/WUSCHEL pathway.

Plants with fea4 mutations, wherein the mutation results in a loss of Fea4 function or loss of Fea4 expression are also called "fea4 plants" or "fea4 null plants". "fea4 null plants" exhibit the "fea4 phenotype" or the "fea4 null phenotype". fea4 plants develop larger meristems during inflorescence and floral shoot development, and ear inflorescence meristems show severe fasciation, suggesting that Fea4 normally acts to limit the growth of these meristems.

Plants with weak fea4 mutations, wherein the mutation results in a partial loss of Fea4 function or partial loss of Fea4 expression are also called "fea4 plants with weak fea4 phenotype". "weak fea4 plants" exhibit the "weak fea4 phenotype". fea4 plants with weak fea4 alleles exhibit similar phenotype as the fea4 null plants, but to a lesser extent. fea4 plants with weak fea4 alleles may also exhibit partial fea4 null phenotype, that is may not exhibit all the fea4 null characteristics. "Weak fea4 alleles" as referred to herein are fea4 variants or variants of SEQ ID NO:1 or 2, which confer weak fea4 phenotype on the plant.

Plants with fea4 mutations that exhibit "null fea4 phenotype" or "weak fea4 phenotype" are referred to herein as plants with "mutant fea4 phenotype".

The term "dominant negative mutation" as used herein refers to a mutation that has an altered gene product that acts antagonistically to the wild-type allele. These mutations usually result in an altered molecular function (often inactive) and are characterized by a "dominant negative" phenotype. A gene variant, a mutated gene or an allele that confers "dominant negative phenotype" would confer a "null" or a "mutated" phenotype on the host cell even in the presence of a wild-type allele.

As used herein, a polypeptide (or polynucleotide) with "FEA4 activity" refers to a polypeptide (or polynucleotide), that when expressed in a "fea4 mutant line" that exhibits the "fea4 mutant phenotype", is capable of partially or fully rescuing the fea4 mutant phenotype.

The terms "gene shuffling" and "directed evolution" are used interchangeably herein. The method of "gene shuffling" consists of iterations of DNA shuffling followed by appropriate screening and/or selection to generate variants of Fea4 nucleic acids or portions thereof having a modified biological activity (Castle et al., (2004) Science 304(5674): 1151-4; U.S. Pat. Nos. 5,811,238 and 6,395,547).

"TILLING" or "Targeting Induced Local Lesions IN Genomics" refers to a mutagenesis technology useful to generate and/or identify, and to eventually isolate mutagenized variants of a particular nucleic acid with modulated expression and/or activity (McCallum et al., (2000), *Plant Physiology* 123:439-442; McCallum et al., (2000) *Nature Biotechnology* 18:455-457; and, Colbert et al., (2001) *Plant Physiology* 126:480-484).

TILLING combines high density point mutations with rapid sensitive detection of the mutations. Typically, ethylmethanesulfonate (EMS) is used to mutagenize plant seed. EMS alkylates guanine, which typically leads to mispairing. For example, seeds are soaked in an about 10-20 mM solution of EMS for about 10 to 20 hours; the seeds are washed and then sown. The plants of this generation are known as M1. M1 plants are then self-fertilized. Mutations that are present in cells that form the reproductive tissues are inherited by the next generation (M2). Typically, M2 plants are screened for mutation in the desired gene and/or for specific phenotypes.

TILLING also allows selection of plants carrying mutant variants. These mutant variants may exhibit modified expression, either in strength or in location or in timing (if the mutations affect the promoter for example). These mutant variants may even exhibit lower FEA4 activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (U.S. Pat. No. 8,071,840).

Other mutagenic methods can also be employed to introduce mutations in the Fea4 gene. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, and N-nitroso-N-ethylurea. Alternatively, ionizing radiation from sources such as X-rays or gamma rays can be used.

Other detection methods for detecting mutations in the Fea4 gene can be employed, e.g., capillary electrophoresis (e.g., constant denaturant capillary electrophoresis and single-stranded conformational polymorphism). In another example, heteroduplexes can be detected by using mismatch repair enzymology (e.g., CELI endonuclease from celery). CELI recognizes a mismatch and cleaves exactly at the 3' side of the mismatch. The precise base position of the mismatch can be determined by cutting with the mismatch repair enzyme followed by, e.g., denaturing gel electrophoresis. See, e.g., Oleykowski et al., (1998) "Mutation detection using a novel plant endonuclease" *Nucleic Acid Res.* 26:4597-4602; and, Colbert et al., (2001) "High-Throughput Screening for Induced Point Mutations" *Plant Physiology* 126:480-484.

The plant containing the mutated fea4 gene can be crossed with other plants to introduce the mutation into another plant. This can be done using standard breeding techniques.

Homologous recombination allows introduction in a genome of a selected nucleic acid at a defined selected position. Homologous recombination has been demonstrated in plants. See, e.g., Puchta et al. (1994), *Experientia* 50: 277-284; Swoboda et al. (1994), *EMBO J.* 13: 484-489; Offringa et al. (1993), *Proc. Natl. Acad. Sci. USA* 90: 7346-7350; Kempin et al. (1997) *Nature* 389:802-803; and, Terada et al., (2002) *Nature Biotechnology*, 20(10):1030-1034).

Methods for performing homologous recombination in plants have been described not only for model plants (Offringa et al. (1990) *EMBO J.* October; 9(10):3077-84) but also for crop plants, for example rice (Terada R, Urawa H, Inagaki Y, Tsugane K, Iida S. *Nat Biotechnol.* 2002; Iida and Terada: *Curr Opin Biotechnol.* 2004 April; 15(2):1328). The nucleic acid to be targeted (which may be FEA4 nucleic acid or a variant thereof as hereinbefore defined) need not be targeted to the locus of FEA4 gene respectively, but may be introduced in, for example, regions of high expression. The nucleic acid to be targeted may be weak fea4 allele or a dominant negative allele used to replace the endogenous gene or may be introduced in addition to the endogenous gene.

Transposable elements can be categorized into two broad classes based on their mode of transposition. These are designated Class I and Class II; both have applications as mutagens and as delivery vectors. Class I transposable elements transpose by an RNA intermediate and use reverse transcriptases, i.e., they are retroelements. There are at least three types of Class I transposable elements, e.g., retrotransposons, retroposons, SINE-like elements. Retrotransposons typically contain LTRs, and genes encoding viral coat proteins (gag) and reverse transcriptase, RnaseH, integrase and polymerase (pol) genes. Numerous retrotransposons have been described in plant species. Such retrotransposons mobilize and translocate via a RNA intermediate in a reaction catalyzed by reverse transcriptase and RNase H encoded by the transposon. Examples fall into the Ty1-copia and Ty3-gypsy groups as well as into the SINE-like and LINE-like classifications (Kumar and Bennetzen (1999) *Annual Review of Genetics* 33:479). In addition, DNA transposable elements such as Ac, Tam1 and En/Spm are also found in a wide variety of plant species, and can be utilized in the invention. Transposons (and IS elements) are common tools for introducing mutations in plant cells.

Plant architecture is dictated by the precise control of meristematic activity. An imbalance in positive or negative maintenance signals can result in a fasciated meristem phenotype. fea4 is a semi-dwarfed mutant with fasciated ears and tassel due to greatly enlarged inflorescence meristems. Vegetative meristems are also increased in size, accounting for the reduced stature and other vegetative phase defects of the mutant. We mapped fea4 to a 2.7 Mbp region of chromosome 6 containing approximately 30 genes. A bZIP transcription factor in this interval contained an EMS-induced early stop codon in the reference allele. A second allele, originally identified as a modifier of ramosa2, also contained a premature stop codon, confirming the identity of the gene. Subsequently, we isolated additional alleles from EMS and transposon mutagenized stocks. Phylogenetic analysis suggests that Fea4 is orthologous to the *Arabidopsis* gene PERIANTHIA, which has an analogous, but less severe, loss-of-function phenotype. We carried out in situ hybridization to determine the expression pattern of Fea4 through various stages of development. During the vegetative phase, Fea4 is expressed specifically in the peripheral zone of the SAM and in the vasculature of immature leaves. Fea4 is conspicuously excluded from the stem cell niche at the tip of the SAM, excluded from the incipient leaf primordium (P0), and strongly enriched in a domain beneath the P0. This peripheral zone expression pattern is present in various embryonic stages examined, and persists until the SAM undergoes the floral transition. Following transition to reproductive fate, Fea4 is expressed throughout the entire inflorescence meristem of the tassel and ear, and also throughout the spikelet-pair, spikelet, and floral meristems. Similar to the pattern observed in the SAM, Fea4 is down regulated at the site of incipient later organ formation in reproductive meristems. Expression of a YFP-FEA4 translational fusion protein under control of the native Fea4 promoter recapitulated the pattern of expression observed by in situ hybridization. Strong nuclear expression was observed in all stages of meristem examined, from embryo to inflorescence, and was also detected in young leaves surrounding the SAM. We have profiled transcriptional changes in 1 mm ears of mutants relative to wild-type by RNA-seq transcriptome profiling, and are beginning to explore potential targets. Genetic analysis suggests that Fea4 functions in parallel to the fea2-td1 (CLAVATA) pathway, suggesting that it defines a novel pathway in meristem size regulation.

EMBODIMENTS

In one embodiment, the fea4 variant that can be used in the methods of the current invention is one or more of the following FEA4 nucleic acid variants: (i) a portion of a Fea4 nucleic acid sequence (SEQ ID NO:1 or 2); (ii) a nucleic acid sequence capable of hybridizing with a Fea4 nucleic acid sequence (SEQ ID NO:1 or 2); (iii) a splice variant of a Fea4 nucleic acid sequence (SEQ ID NO:1 or 2); (iv) a naturally occurring allelic variant of a Fea4 nucleic acid sequence (SEQ ID NO:1 or 2); (v) a fea4 nucleic acid sequence obtained by gene shuffling; (vi) a fea4 nucleic acid sequence obtained by site-directed mutagenesis; (vii) a fea4 variant obtained and identified by the method of TILLING.

In one embodiment, the levels of endogenous Fea4 expression can be decreased in a plant cell by antisense constructs, sense constructs. RNA silencing constructs, RNA interference, artificial microRNAs and genomic disruptions. Examples of genomic disruption include, but are not limited to, disruptions induced by transposons, tilling, homologous recombination.

In one embodiment, a modified plant miRNA precursor may be used, wherein the precursor has been modified to replace the miRNA encoding region with a sequence designed to produce a miRNA directed to Fea4. The precursor is also modified in the star strand sequence to correspond to changes in the miRNA encoding region.

In one embodiment, a nucleic acid variant of Fea4 useful in the methods of the invention is a nucleic acid variant obtained by gene shuffling.

In one embodiment, a genetic modification may also be introduced in the locus of a maize Fea4 gene using the technique of TILLING (Targeted Induced Local Lesions In Genomes).

In one embodiment, site-directed mutagenesis may be used to generate variants of Fea4 nucleic acids. Several methods are available to achieve site-directed mutagenesis; the most common being PCR based methods (U.S. Pat. No. 7,956,240).

In one embodiment homologous recombination can also be used to inactivate, or reduce the expression of endogenous Fea4 gene in a plant.

Homologous recombination can be used to induce targeted gene modifications by specifically targeting the Fea4 gene in vivo. Mutations in selected portions of the fea4 gene sequence (including 5' upstream, 3' downstream, and intragenic regions) such as those provided herein are made in vitro and introduced into the desired plant using standard techniques. Homologous recombination between the introduced mutated fea4 gene and the target endogenous FEA4 gene would lead to targeted replacement of the wild-type gene in transgenic plants, resulting in suppression of Fea4 expression or activity.

In one embodiment, catalytic RNA molecules or ribozymes can also be used to inhibit expression of FEA4 gene. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the constructs. A number of classes of ribozymes have been identified. For example, one class of ribozymes is derived from a number of small circular RNAs that are capable of self-cleavage and replication in plants. The RNAs can replicate either alone (viroid RNAs) or with a helper virus (satellite RNAs). Examples of RNAs include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes has been described. See, e.g., Haseloff et al. (1988) *Nature*, 334:585-591.

Another method to inactivate the Fea4 gene is by inhibiting expression is by sense suppression. Introduction of expression cassettes in which a nucleic acid is configured in the sense orientation with respect to the promoter has been shown to be an effective means by which to block the transcription of a desired target gene (Napoli et al. (1990), *The Plant Cell* 2:279-289; and U.S. Pat. Nos. 5,034,323, 5,231,020, and 5,283,184).

In one embodiment, the Fea4 gene can also be inactivated by, e.g., transposon based gene inactivation.

In one embodiment, the inactivating step comprises producing one or more mutations in the Fea4 gene sequence, where the one or more mutations in the Fea4 gene sequence comprise one or more transposon insertions, thereby inactivating the Fea4 gene compared to a corresponding control plant. For example, the mutation may comprise a homozygous disruption in the Fea4 gene or the one or more mutations comprise a heterozygous disruption in the Fea4 gene.

These mobile genetic elements are delivered to cells, e.g., through a sexual cross, transposition is selected for and the resulting insertion mutants are screened, e.g., for a phenotype of interest. Plants comprising disrupted Fea4 genes can be crossed with a wild-type plant. Any of a number of standard breeding techniques can be used, depending upon the species to be crossed. The location of a TN (transposon) within a genome of an isolated or recombinant plant can be determined by known methods, e.g., sequencing of flanking regions as described herein. For example, a PCR reaction from the plant can be used to amplify the sequence, which can then be diagnostically sequenced to confirm its origin. Optionally, the insertion mutants are screened for a desired phenotype, such as the inhibition of expression or activity of Fea4 or alteration of an agronomic characteristic.

EXAMPLES

The present invention is further illustrated in the following Examples, in which parts and percentages are by weight and degrees are Celsius, unless otherwise stated. It should be understood that these examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Cloning of Maize fea4 Gene

The fea4-0 allele was discovered in an M2 screen of an EMS mutagenized A619 Inbred population.

Figure 1A:
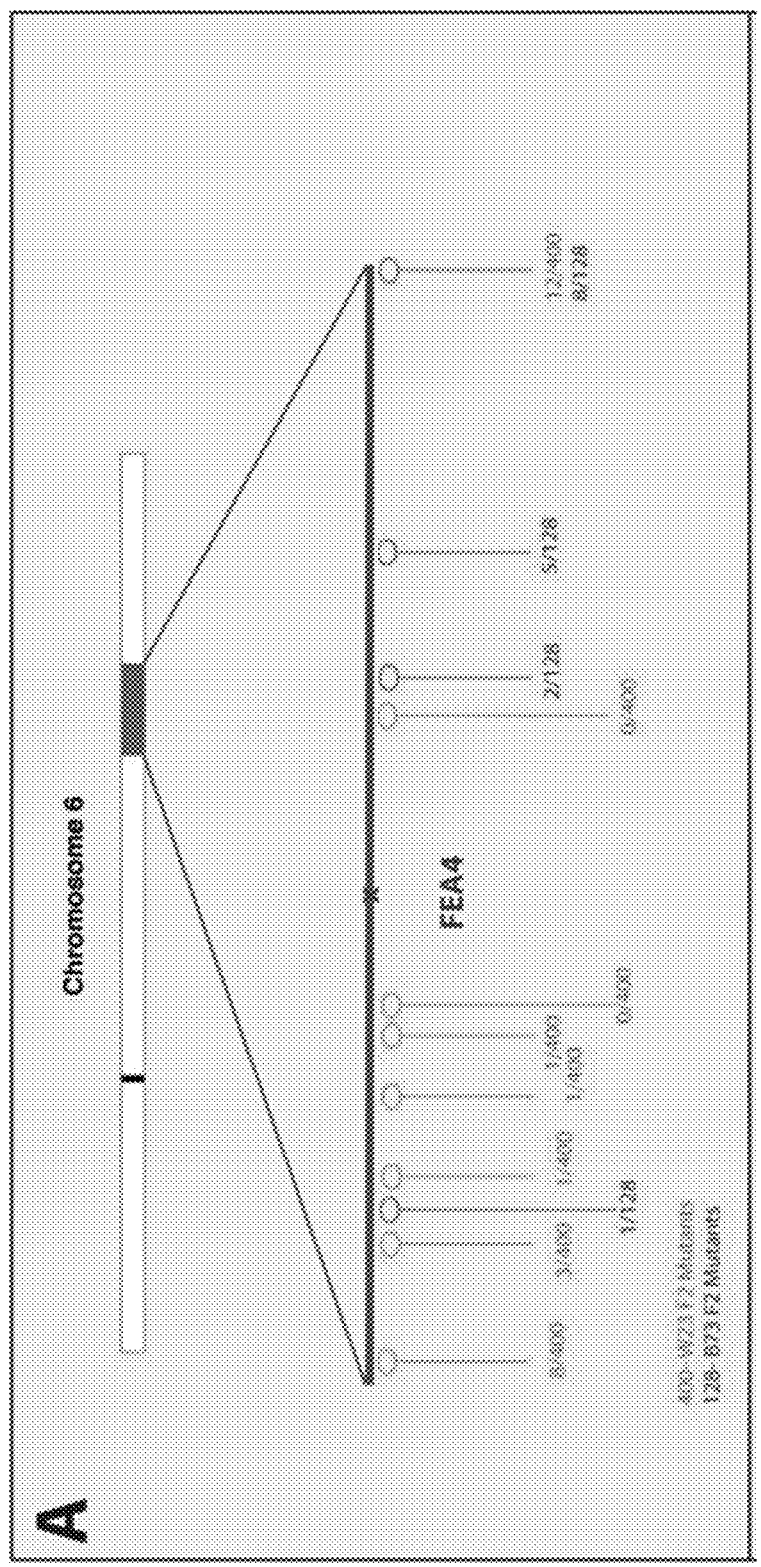
Figure 1B:
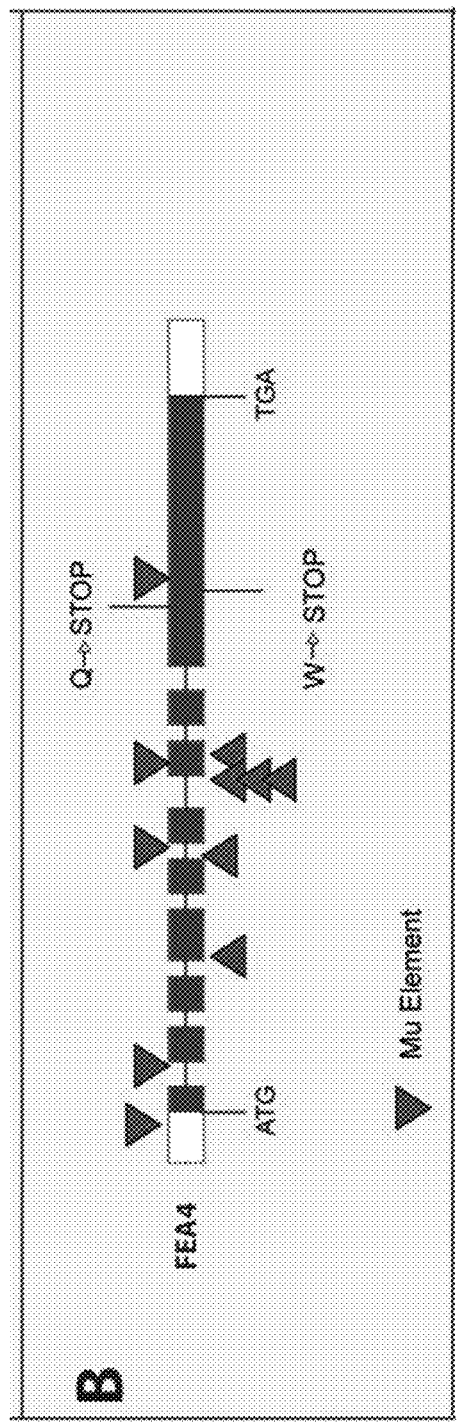
Figure 1C:
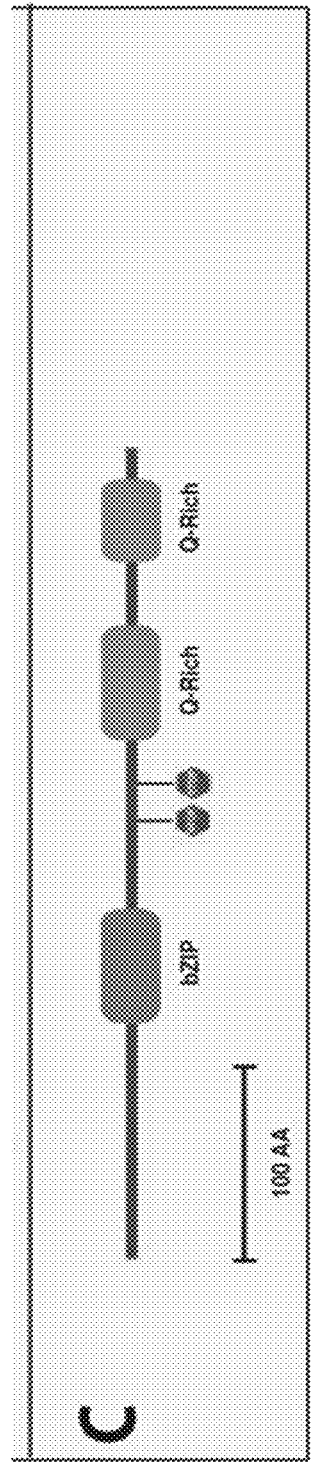

Two F2 mapping populations were created by crossing fea4-0 (A619) to the B73 and W23 inbred lines. The mutation was mapped to a 2.7 Mbp region (FIG. 1A), which contained approximately 30 annotated genes. A candidate in this region was selected based on its expression in developing ear primordia. Sequencing of a candidate bZIP transcription factor revealed an EMS Induced (C-to-T) transition causing a premature stop codon (FIG. 1B). A second allele, fea4-rel*09-5171, also contained an early stop codon, confirming the identity of the gene. Subsequently, 11 TUSC insertional mutants In FEA4 were obtained, which are currently being phenotyped. The two stop codons fall after the bZIP domain, but before two glutamine-rich regions (FIG. 1C). These C-terminal motifs have been shown to be important for the regulation of TGA-class bZIP proteins by glutaredoxins.

Example 2

Maize Mutant fea4 Phenotype fea4 is a semi-dwarfed recessive mutant with massively fasciated ears and tassel. Vegetative phenotypes include shorter, wider leaves and reduced plant stature (FIG. 2A). This correlates with an ~33% increase in size of the shoot apical meristem (SAM). After the reproductive transition, fea4 mutants produce thickened tassels with increased spikelet density and increased rachis diameter (FIG. 2B). The mutants bear incredibly fasciated ears that are shorter and more disorganized than wild-type (FIG. 2C). SEM analysis of immature ears reveals that the primary defect is a greatly enlarged inflorescence meristem (FIG. 2D) whereas higher order reproductive meristems do not appear to be affected. FIG. 2E shows the wild-type ear with compact conical inflorescence meristem (Scale bars=1 mm).

Example 3

Interaction Between Meristem Size and Meristem Determinacy

Figure 3A:
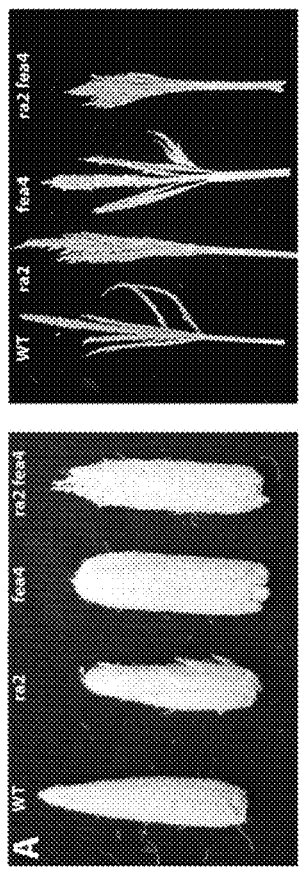

Two alleles of fea4 came from a ramosa2 (ra2) modifier screen. Segregating F2 populations (FIG. 3A) showed that ra2 suppresses the fasciation phenotype of fea4 and causes repeated bifurcation or splitting of the ear inflorescence meristem.

Figure 3B:
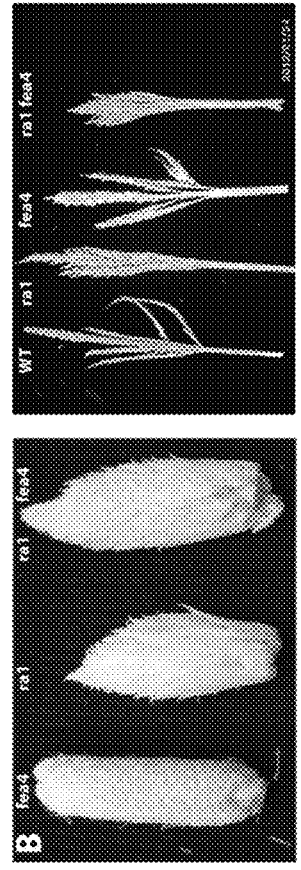

FIG. 3B shows the double mutants of fea4 and ramosa1. Ramosa1 appears to suppress fea4, suggesting that fea4 acts upstream of this enforcer of spikelet pair meristem determinacy.

Figure 3C:
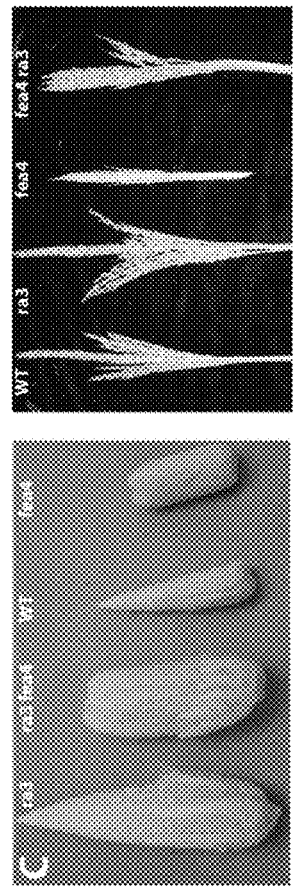
Figure 5:
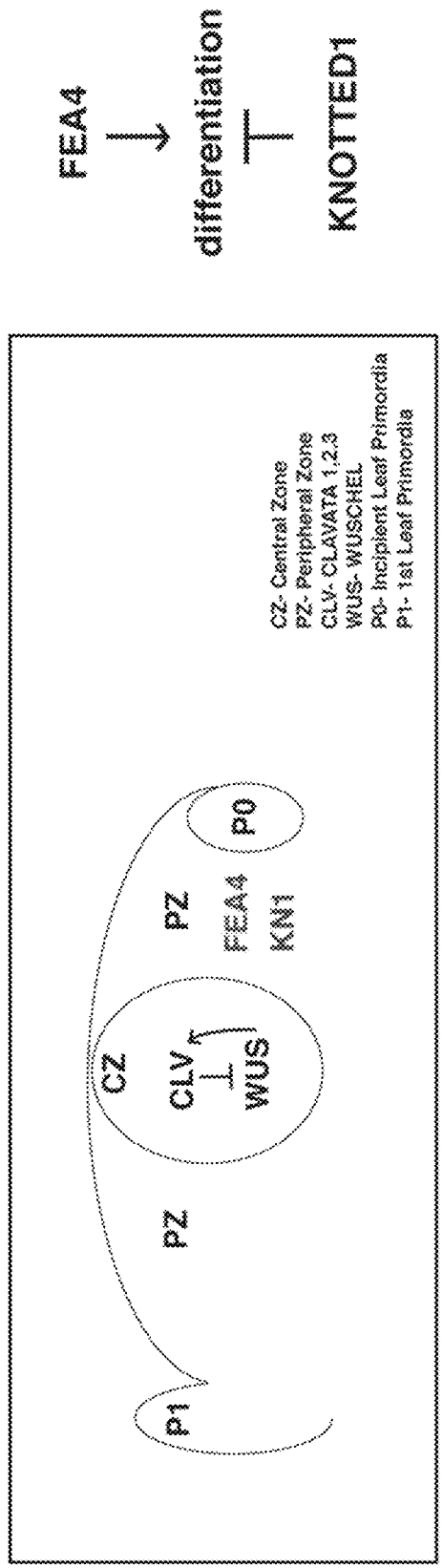
FIG. 5 shows a proposed model of the fea4 pathway.

Double mutants of fea4 and ramosa3 appeared to be entirely additive, indicating that these factors may act in independent pathways (FIG. 3C).

Example 4 fea2/fea4 Double Mutant Analysis

Double mutants of fea4 and the CLAVATA2 ortholog display synergistic defects in reproductive (FIG. 4A) and vegetative development (FIG. 4B). This can be interpreted to mean that fea4 functions in parallel to the stem cell niche controlling pathway, likely outside of the central zone.

Example 5

Expression Analysis of fea4 Gene

We carried out in situ hybridization to determine the expression pattern of Fea4 through various stages of development. During the vegetative phase, Fea4 is expressed specifically in the peripheral zone of the SAM and in the vasculature of immature leaves. Fea4 is conspicuously excluded from the stem cell niche at the tip of the SAM, excluded from the incipient leaf primordium (P0), and strongly enriched in a domain beneath the P0. This peripheral zone expression pattern is present in various embryonic stages examined, and persists until the SAM undergoes the floral transition. Following transition to reproductive fate, Fea4 is expressed throughout the entire inflorescence meristem of the tassel and ear, and also throughout the spikelet-pair, spikelet, and floral meristems. Similar to the pattern observed in the SAM, Fea4 is down regulated at the site of incipient later organ formation in reproductive meristems.

Example 6

Expression of Yellow Fluorescent Fusion Protein from the FEA4 Promoter

A recombinant DNA construct was made to allow for in vivo localization of FEA4 that has been tagged with Yellow Fluorescent Protein (YFP). The construct contained the following elements in the 5' to 3' orientation: 1) FEA4 Promoter; 2) YFP-FEA4 fusion protein coding region; and 3) FEA4 3'-UTR. Transgenic maize plants containing this recombinant DNA construct were produced. Expression of a YFP-FEA4 translational fusion protein under control of the native promoter recapitulated the pattern of expression observed by in situ hybridization. Strong nuclear expression was observed in all stages of meristem examined, from embryo to inflorescence, and was also detected in young leaves surrounding the SAM.

Example 7

Reduced Stamen Number in fea4 Plants

Floral organs were analyzed for fea4 mutant plants in an A619 background. Floral organ numbers (stamens) were counted in 50 florets of fea4 mutant and 50 florets of wild-type A619 siblings. 100% of florets contained 3 stamens in wild-type samples, whereas 23% of mutant florets contained only 2 stamens (FIG. 6A-FIG. 6D).

Example 8

YFP-FEA4 Fusion Construct Rescues the fea4 Mutant

To examine the subcellular and tissue-scale localization of the FEA4 protein product, a translational fusion was constructed containing the yellow fluorescent protein (YFP) fused to the FEA4 coding sequence, under control of the native promoter. The construct contained the following elements in the 5' to 3' orientation: 1) FEA4 Promoter; 2) YFP-FEA4 fusion protein coding region; and 3) FEA4 3'-UTR. This construct was transformed into the Hill inbred maize background, and backcrossed twice to the fea4 mutant to assess complementation. The presence of this transgene was sufficient to rescue the mutant phenotype in two independent events, indicating that the fusion protein is functional in planta (n=40 plants in segregating families). This experiment provided independent confirmation of the identity of the gene underlying the mutant phenotype. It also confirmed that the 1 kb promoter and downstream UTR sequences drive expression in the required domain. Additionally, this experiment demonstrated that the YFP-tag does not interfere with the function of the FEA4 protein.

Example 9 fea4 and fea2 Interact Synergistically to Control Meristem Size

F2 populations were created segregating for fea4 and fasicated ear2 (fea2); fea2 is the maize ortholog of CLAVATA2. Double mutants displayed a wide range of synergistic phenotypes in vegetative and reproductive structures.

To quantitate the genetic interaction, we genotyped plants from a segregating family, and measured the size of the shoot apical meristem (SAM) at 14 days after planting. The SAM size was increased by approximately 30% in the fea2 and fea4 single mutants relative to wild-type, and by 122% in the fea2/fea4 double mutants. The results are shown in Table 1.

TABLE 1

| Line | Meristem Size (μm) | Standard Deviation |
| --- | --- | --- |
| Wild-Type | 156.1 | 10.5 |
| fea2 | 205.6 | 9.7 |
| fea4 | 202.5 | 21.3 |
| fea2/fea4 | 347.3 | 70.9 |

Example 10

Additional fea4 Mutants

Additional fea4 mutant lines were created by EMS mutagenesis of an inbred maize line. Mutant lines fea4-33 and fea4-269 were analyzed. The fea4-33 mutant line has a C-to-T change at position 1952 that changes a glutamine residue to a stop codon. Mutant line fea4-369 has a G-to-A change at position 1902 that changes a glycine residue to a serine residue.

What is claimed is:

1. A method of making a maize plant in which expression of an endogenous FEA4 gene, which encodes a polypeptide having an amino acid sequence of at least 98% identity, based on the Clustal W method of alignment, when compared to SEQ ID NO: 3, is reduced relative to a control maize plant, the method comprising the steps of:
   a. introducing a mutation into the endogenous FEA4 gene; and
   b. detecting the mutation and wherein the maize plant comprising the mutant FEA4 gene has reduced plant height, increased kernel rows, and altered tassel branching, as compared to a wild type maize plant.

2. The method of claim 1 wherein steps (a) and (b) are done using a Targeting Induced Local Lesions IN Genomics (TILLING) method and wherein the mutation is effective in reducing the expression of the endogenous Fea4 gene or its activity.

3. The method of claim 1 wherein the mutation is a site-specific mutation.

4. The method of claim 1, wherein the mutation comprises a transposon inserted into the FEA4 gene sequence.

* * * * *